United States Patent
Harrold et al.

(10) Patent No.: US 9,804,066 B2
(45) Date of Patent: *Oct. 31, 2017

(54) SIMULTANEOUS ACQUISITION OF BIOMETRIC DATA AND NUCLEIC ACID

(71) Applicant: LIFE TECHNOLOGIES CORPORATION, Carlsbad, CA (US)

(72) Inventors: Michael Harrold, San Mateo, CA (US); Lori Hennessy, San Mateo, CA (US); Jason Yingjie Liu, Foster City, CA (US); Chang Zhong, Stanford, CA (US)

(73) Assignee: LIFE TECHNOLOGIES CORPORATION, Carlsbad, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/739,899

(22) Filed: Jun. 15, 2015

(65) Prior Publication Data

US 2016/0011085 A1    Jan. 14, 2016

Related U.S. Application Data

(63) Continuation of application No. 13/624,799, filed on Sep. 21, 2012, now Pat. No. 9,058,646.

(60) Provisional application No. 61/538,238, filed on Sep. 23, 2011.

(51) Int. Cl.

| | | |
|---|---|---|
| *C12Q 1/68* | (2006.01) | |
| *C12M 1/00* | (2006.01) | |
| *C12M 1/34* | (2006.01) | |
| *G01N 1/30* | (2006.01) | |
| *G06T 7/00* | (2017.01) | |
| *A61B 5/15* | (2006.01) | |
| *A61B 5/151* | (2006.01) | |
| *A61B 5/00* | (2006.01) | |
| *A61B 5/1172* | (2016.01) | |
| *A61B 5/145* | (2006.01) | |
| *G06K 9/00* | (2006.01) | |
| *A61B 10/00* | (2006.01) | |
| *A61B 10/02* | (2006.01) | |
| *A61B 5/157* | (2006.01) | |

(52) U.S. Cl.
CPC ............ *G01N 1/30* (2013.01); *A61B 5/0077* (2013.01); *A61B 5/1172* (2013.01); *A61B 5/1411* (2013.01); *A61B 5/14514* (2013.01); *A61B 5/150022* (2013.01); *A61B 5/150083* (2013.01); *A61B 5/150091* (2013.01); *A61B 5/15105* (2013.01); *A61B 5/15134* (2013.01); *A61B 5/150412* (2013.01); *A61B 5/150984* (2013.01); *A61B 10/0064* (2013.01); *A61B 10/0233* (2013.01); *G06K 9/00013* (2013.01); *G06K 9/00543* (2013.01); *G06T 7/0012* (2013.01); *A61B 5/157* (2013.01); *G06K 2009/00946* (2013.01)

(58) Field of Classification Search
CPC ....... G06T 7/0012; A61B 5/1411; C12Q 1/68; G06K 9/00
USPC .................... 435/6.1, 283.1, 287.2; 382/124; 422/430; 600/562, 573
See application file for complete search history.

(56) References Cited

U.S. PATENT DOCUMENTS

| | | |
|---|---|---|
| 2,151,733 A | 3/1939 | Bonfield |
| 4,190,056 A | 2/1980 | Tapper et al. |
| 6,355,439 B1 | 3/2002 | Chung et al. |
| 6,643,531 B1 | 11/2003 | Katarow |
| 6,659,038 B2 | 12/2003 | Calcagno |
| 7,308,123 B2 | 12/2007 | Fenrich et al. |
| 7,587,793 B2 | 9/2009 | Sangha |
| 7,906,192 B2 | 3/2011 | Calcagno |
| 8,009,882 B2 | 8/2011 | Fenrich et al. |
| 8,041,084 B2 | 10/2011 | Fenrich et al. |
| 8,307,854 B1 | 11/2012 | Vu et al. |
| 9,058,646 B2 | 6/2015 | Harrold et al. |
| 2002/0073340 A1 | 6/2002 | Mambakkam et al. |
| 2002/0183624 A1 | 12/2002 | Rowe et al. |
| 2006/0074280 A1 | 4/2006 | Martis et al. |
| 2008/0194041 A1 | 8/2008 | Guirguis |
| 2008/0214942 A1 | 9/2008 | Oh et al. |
| 2009/0227897 A1 | 9/2009 | Wendt et al. |
| 2010/0030111 A1 | 2/2010 | Perriere et al. |
| 2010/0041131 A1 | 2/2010 | Brown |
| 2010/0098831 A1 | 4/2010 | Anderson et al. |
| 2010/0184126 A1 | 7/2010 | Rutty et al. |

(Continued)

FOREIGN PATENT DOCUMENTS

| | | |
|---|---|---|
| DE | 202005020535 | 5/2006 |
| WO | 9907282 | 2/1999 |
| WO | 2006061771 | 6/2006 |
| WO | 2009021130 | 2/2009 |
| WO | 2011026169 | 3/2011 |

OTHER PUBLICATIONS

Kopka, et al., "New Optimized DNA Extraction Protocol for Fingerprints Deposited on a Special Self-Adhesive Security Seal and Other Latent Samples Used for Human Identification," J. Forensic Sci., Technical Note-Criminalistics, 2011, pp. 1-6.

(Continued)

*Primary Examiner* — Narayan Bhat
(74) *Attorney, Agent, or Firm* — Peter G. Foiles

(57) ABSTRACT

Systems, methods, and kits are disclosed for collection, labeling and analyzing biological samples containing nucleic acid in conjunction with collecting at least one ridge and valley signature of an individual. Such devices and methods are used in forensic, human identification, access control and screening technologies to rapidly process an individual's identity or determine the identity of an individual.

17 Claims, 20 Drawing Sheets

(56) References Cited

U.S. PATENT DOCUMENTS

| | | |
|---|---|---|
| 2010/0191147 A1 | 7/2010 | Miyoshi et al. |
| 2011/0163163 A1 | 7/2011 | Rowe |
| 2011/0172510 A1 | 7/2011 | Chickering et al. |
| 2012/0103421 A1 | 5/2012 | Grenz et al. |
| 2012/0165697 A1 | 6/2012 | Kelly et al. |
| 2013/0078625 A1 | 3/2013 | Holmes et al. |
| 2013/0106568 A1 | 5/2013 | Harrold et al. |
| 2013/0202182 A1 | 8/2013 | Rowe et al. |
| 2013/0324865 A1 | 12/2013 | Yavelov et al. |
| 2016/0154990 A1* | 6/2016 | Harrold ............... A61B 5/1172 382/116 |

OTHER PUBLICATIONS

Mullis, et al. "The Polymerase Chain Reaction" Birkhauser, Boston, 1994.
Standring, S., "Grays Anatomy: The Anatomical Basis of Clinical Practice" 40th edition, 2008.
Wang, Y. et al. "Data Acquisition and Quality Analysis of 3-Demensional Fingerprints" Florida: IEEE conference on Biometrics, Identity and Security. http://vis.uky.edu/~realtime3d/Doc/3D_Fingerprint_Quality.pdf, Retrieved Mar. 2000, 10 pages.
Wang, Y. et al. "Fit-sphere unwrapping and performance analysis of 3D fingerprints" Optical Society of America, vol. 49, 2010, pp. 592-600.

* cited by examiner

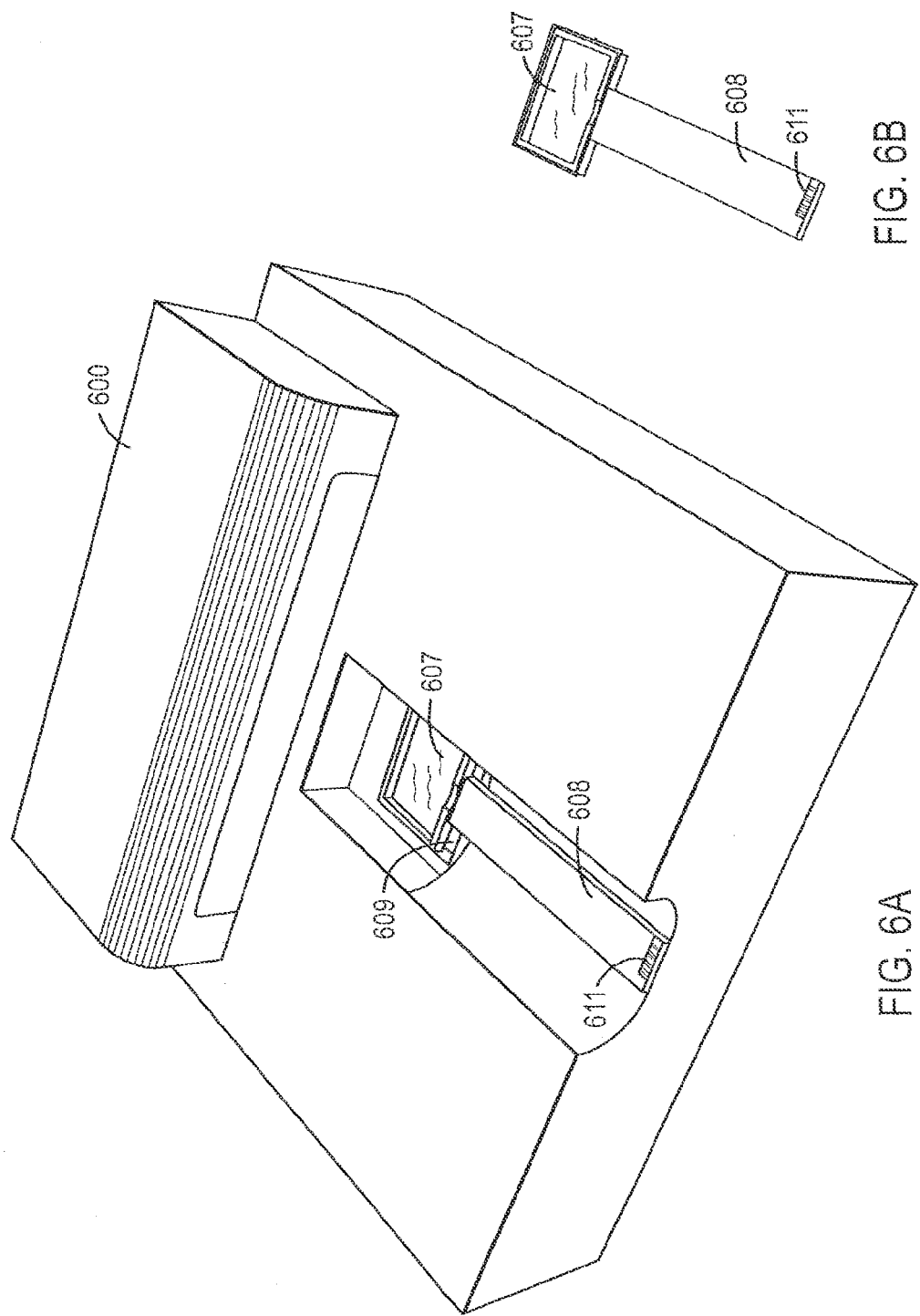

SIMULTANEOUS ACQUISITION OF BIOMETRIC DATA AND NUCLEIC ACID

This application is a continuation of U.S. patent application Ser. No. 13/624,799 filed Sep. 21, 2012, which claims the benefit of priority under 35 U.S.C. §119(e) to U.S. Provisional Application No. 61/538,238 filed Sep. 23, 2011, the disclosure of which is incorporated by reference in its entirety.

The section headings used herein are for organizational purposes only and should not be construed as limiting the subject matter described herein in any way.

FIELD

The present teachings relate to devises and methods for obtaining biometric data and nucleic acids for use in human identification and forensic science.

INTRODUCTION

Forensic evidence and biometric data are often used together to identify perpetrators of criminal activities as well as for the identification of missing persons, victims of mass disasters, paternity testing and to exonerate the innocent. The ability to simultaneously collect biometric data such as fingerprints, an iris or retinal scan, an image or photo of an individual can, with a biological sample(s) such as forensic evidence including but not limited to blood, tissue, hair, body fluid or a buccal sample, provide a system for expediting identification, access control, and screening of individuals. Furthermore, maintaining identification of related data points and correlating the data with the respective biological samples can be complicated and susceptible to errors which compromise the chain of custody. Therefore, there remains a need to accurately collect, associate correctly, and process biometric data and biological samples from a single individual in one collection step or workflow.

SUMMARY

In a first aspect, a system is provided for collection of a biological sample including a nucleic acid sample and at least one ridge and valley signature of an individual including at least a first imaging component including a scanning surface configured to permit an energy wave to penetrate the scanning surface, where the energy wave is configured to image the at least one ridge and valley signature of an appendage of the individual; and a substrate configured to collect the biological sample from an appendage of the individual; where the scanning surface and the substrate are configured to permit collecting the at least one ridge and valley signature of the appendage while the appendage is positioned upon the scanning surface and in contact with the substrate and to permit collecting the biological sample as the appendage is withdrawn from the scanning surface. In various embodiments, the system may be configured to collect the biological sample and the at least one ridge and valley signature simultaneously. In some embodiments, the appendage may be a finger, toe, palm of a hand or sole of a foot.

In various embodiments, the at least first imaging component may be an optical scanner or a capacitance scanner. In various embodiments, the at least first imaging component is selected from a camera, an active pixel imager, a CMOS imager, an imager that images in multiple wavelengths, a CCD camera, a photo detector array, and a TFT imager. In some embodiments, the at least one ridge and valley signature is collected electronically. In some embodiments, the optical scanner includes a LED, laser diode, incandescent light source, or a multispectral imager.

In various embodiments, the scanning surface may be formed from a material selected from a plastic, a polyolefin, a polystyrene, a metal, a metal alloy, a glass, a silicon or combinations thereof. The material of the scanning surface may be transparent or translucent.

The system may further include a support for the substrate configured to permit the collection of the at least one ridge and valley signature through the support.

In some embodiments, the appendage may be in direct contact with the support and in operational contact with the scanning surface. The support may be formed from a material selected from a polymer, a metal, a metal alloy, a glass, a silicon or combinations thereof. In some embodiments, the support is transparent or translucent.

In various embodiments, the substrate may include a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof. In some embodiments, the paper material further includes a lysis solution. In various embodiments, the lysis solution includes proteinase K. In various embodiments, the lysis solution includes an enzyme selected from a serine protease, a cysteine protease, an acid protease, a metalloprotease, an aminopeptidase, a carboxypeptidase, a pancreatic proteolytic enzyme and a keratinase. In some embodiments, the paper material further includes microneedles.

In other embodiments, the substrate may be a starch, an agarose, an alginate, a carrageenan or a synthetic polymer gel, or a mixture thereof.

In some embodiments, the substrate may include an identifier to associate the biological sample of the individual with the at least one ridge and valley signature of the individual, where the identifier is alphanumeric, graphical, magnetic, or electromagnetic. In some embodiments, the substrate identifier may be a barcode. In some embodiments, the support may include an identifier to associate the biological sample of the individual with the at least one ridge and valley signature of the individual, where the identifier is alphanumeric, graphical, magnetic, or electromagnetic. In some embodiments, the support identifier may be a barcode.

In some embodiments, at least a portion of the support may be positioned over the scanning surface and may be transparent or translucent. In some embodiments, the substrate is positioned proximal to the scanning surface. In some embodiments, the transparent support may be attached to the substrate, wherein at least a portion of the transparent support is positioned over the scanning surface and at least a portion of the substrate is positioned proximal to the substrate. In some embodiments, both substrate and support are positioned over the scanning surface.

The system may further include a processor configured to transmit the ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control and any combination thereof.

In various embodiments, the substrate is configured for archiving the biological sample or for shipping the sample to another location for testing. In various embodiments, the support is configured for archiving the biological sample or for shipping the sample to another location for testing.

The system may further include at least a second imaging component for collecting at least a second image of the individual, selected from a facial image, an iris image, a retinal image or an ear image of the individual. In some embodiments, an identifier further associates the at least second image of the individual with the biological sample and the at least one ridge and valley signature of the individual.

The system may further include one or more additional components selected from an amplification component, a purification component, a separation component or any combination thereof. The additional components may be configured to perform one or more of the following: obtain the at least one nucleic acid from the biological sample; purify the at least one nucleic acid before further amplification and analysis; amplify the at least one nucleic acid; separate the amplified at least one nucleic acid; and/or detect the amplified at least one nucleic acid.

In another aspect, a method is provided for collecting a biological sample including at least one nucleic acid and at least one ridge and valley signature of an individual, including: providing at least a first imaging component configured to provide an energy wave and including a scanning surface configured to permit the energy wave to penetrate the scanning surface; providing a substrate configured to collect the biological sample from an appendage of the individual; positioning an appendage of the individual upon the scanning surface and in contact with the substrate; collecting the at least one ridge and valley signature from the appendage imaged by the energy wave; and withdrawing the appendage from the scanning surface, thereby collecting the biological sample. In some embodiments, the steps of collecting the biological sample and collecting the at least one ridge and valley signature are performed simultaneously. In some embodiments, the appendage may be a finger, toe, palm of a hand or sole of a foot.

The method may further include the step of vibrating the substrate as the appendage is withdrawn.

The method may further include the step of transmitting the at least one ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier to associate the biological sample of the individual with the at least one ridge and valley signature of the individual, where the identifier is alphanumeric, graphical, magnetic, or electromagnetic. In various embodiments, the identifier is a barcode.

The method may further include the step of subjecting the biological sample to at least one of a polymerase chain reaction, a DNA sequencing reaction, STR analysis, SNP analysis, or Indel analysis. In some embodiments, the at least one nucleic acid of the collected biological sample is not isolated or purified before being subjected to at least one of a polymerase chain reaction, a DNA sequencing reaction, STR analysis, SNP analysis, or Indel analysis.

The method may further include the step of archiving the substrate containing the biological sample.

The method may also include the step of collecting at least a second image of the individual, selected from a facial image, an iris image, a retinal image or an ear image of the individual. In some embodiments, an identifier associates the at least second image with the biological sample and the at least one ridge and valley signature of the individual.

In various embodiments, the at least first imaging component may be an optical scanner or a capacitance scanner. In various embodiments, the at least first imaging component is selected from a camera, an active pixel imager, a CMOS imager, an imager that images in multiple wavelengths, a CCD camera, a photo detector array, and a TFT imager. In some embodiments, the at least one ridge and valley signature is collected electronically. In some embodiments, the optical scanner includes a LED, laser diode, incandescent light source, or a multispectral imager.

In various embodiments, the scanning surface is formed from a material selected from a plastic, a polyolefin, a polystyrene, a metal, a metal alloy, a glass, a silicon or combinations thereof. In some embodiments, the material of the scanning surface is transparent or translucent.

In various embodiments, the substrate includes a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof. In some embodiments, the paper material further includes a lysis solution. In various embodiments, the lysis solution includes proteinase K. In various embodiments, the lysis solution includes an enzyme selected from a serine protease, a cysteine protease, an acid protease, a metalloprotease, an aminopeptidase, a carboxypeptidase, a pancreatic proteolytic enzyme and a keratinase. In some embodiments, the paper material further includes microneedles.

In various embodiments, the substrate includes a gel. In various embodiments, the gel may be a starch, agarose, alginate, carrageenan or synthetic polymer gel, or a mixture thereof. In some embodiments, the gel may be configured to permit electrophoresis.

The method may further include the step of electrophoresing the biological sample on the gel to concentrate the at least one nucleic acid.

In various embodiments, the substrate further includes a support. In various embodiments, the support may be formed from a material selected from a polymer, a metal, a metal alloy, a glass, a silicon material or combination thereof. In some embodiments, the support may be transparent or translucent.

In various embodiments, at least a portion of the substrate is positioned upon the scanning surface and is transparent or translucent. In various embodiments, at least a portion of the support is positioned upon the scanning surface and is transparent or translucent. In various embodiments, at least a portion of the substrate is positioned proximal to the scanning surface. In various embodiments, the collection of the at least one ridge and valley signature may be made through the support, wherein the appendage is in direct contact with the support and operational contact with the scanning surface.

In another aspect, a system is provided for collection of a biological sample including at least one nucleic acid sample and at least one ridge and valley signature of an individual including: at least a first imaging component including: a scanning surface configured to permit an energy wave to penetrate the scanning surface, where the energy wave is configured to image the at least one ridge and valley signature of an appendage of the individual; a support for a lysis solution; and a lysis solution configured to collect the biological sample; where the imaging component is configured to permit capturing the ridge and valley signature through the scanning surface, the support and the lysis solution.

In various embodiments, the scanning surface may be formed from a material selected from a plastic, a polyolefin, a polystyrene, a metal, a metal alloy, a glass, a silicon or combinations thereof. The material of the scanning surface may be transparent or translucent.

In various embodiments, the support may be transparent or translucent to the energy wave. In various embodiments, the support is formed from a material selected from a polymer, a metal, a metal alloy, a glass, a silicon material or combination thereof. In various embodiments, the lysis solution may be transparent or translucent to the energy wave. In various embodiments, the lysis solution may include proteinase K. In various embodiments, the lysis solution may include an enzyme selected from a serine protease, a cysteine protease, an acid protease, a metalloprotease, an aminopeptidase, a carboxypeptidase, a pancreatic proteolytic enzyme and a keratinase.

In various embodiments, the at least first imaging component may be an optical scanner or a capacitance scanner. In various embodiments, the at least first imaging component may be selected from a camera, an active pixel imager, a CMOS imager, an imager that images in multiple wavelengths, a CCD camera, a photo detector array, and a TFT imager. In some embodiments, the at least one ridge and valley signature may be collected electronically. In some embodiments, the optical scanner may include a LED, laser diode, incandescent light source, or a multispectral imager. In various embodiments, the system may be configured to collect the biological sample and the at least one ridge and valley signature simultaneously.

The system may further include a processor configured to transmit the ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control and any combination thereof.

The system may further include at least a second imaging component for collecting at least a second image of the individual, selected from a facial image, an iris image, a retinal image or an ear image of the individual. In some embodiments, an identifier further associates the at least second image of the individual with the biological sample and the at least one ridge and valley signature of the individual.

The system may further include one or more additional components selected from an amplification component, a purification component, a separation component or any combination thereof. The additional components may be configured to perform one or more of the following: obtain the at least one nucleic acid from the biological sample; purify the at least one nucleic acid before further amplification and analysis; amplify the at least one nucleic acid; separate the amplified at least one nucleic acid; and/or detect the amplified at least one nucleic acid.

In another aspect, a method is provided for collecting a biological sample including at least one nucleic acid sample and at least one ridge and valley signature of an individual including the steps of: providing at least a first imaging component configured to provide an energy wave, where the at least a first imaging component includes a scanning surface, a support for a lysis solution, and a lysis solution configured to collect the biological sample, where the scanning surface is configured to permit the energy wave to penetrate the scanning surface, the support and the lysis solution; positioning an appendage of the individual in the lysis solution in the support; collecting at least one ridge and valley signature of the appendage; and collecting the biological sample in the lysis solution from the support. In various embodiments, the steps of collecting the biological sample and collecting the at least one ridge and valley signature may be performed simultaneously.

In various embodiments, the support may be transparent or translucent to the energy wave. In various embodiments, the support is formed from a material selected from a polymer, a metal, a metal alloy, a glass, a silicon material or combination thereof. In various embodiments, the lysis solution may be transparent or translucent to the energy wave. In various embodiments, the lysis solution may include proteinase K. In various embodiments, the lysis solution may include an enzyme selected from a serine protease, a cysteine protease, an acid protease, a metalloprotease, an aminopeptidase, a carboxypeptidase, a pancreatic proteolytic enzyme and a keratinase.

In various embodiments, the at least first imaging component may be an optical scanner or a capacitance scanner. In various embodiments, the at least first imaging component may be selected from a camera, an active pixel imager, a CMOS imager, an imager that images in multiple wavelengths, a CCD camera, a photo detector array, and a TFT imager. In some embodiments, the at least one ridge and valley signature may be collected electronically. In some embodiments, the optical scanner may include a LED, laser diode, incandescent light source, or a multispectral imager.

The method may further include the step of transmitting the at least one ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier to associate the biological sample of the individual with the at least one ridge and valley signature of the individual, where the identifier is alphanumeric, graphical, magnetic, or electromagnetic. In various embodiments, the identifier may be a barcode.

The method may further include the step of subjecting the biological sample to at least one of a polymerase chain reaction, a DNA sequencing reaction, STR analysis, SNP analysis, or Indel analysis. In some embodiments, the at least one nucleic acid of the collected biological sample may not be isolated or purified before being subjected to at least one of a polymerase chain reaction, a DNA sequencing reaction, STR analysis, SNP analysis, or Indel analysis.

The method may also include the step of collecting at least a second image of the individual, selected from a facial image, an iris image, a retinal image or an ear image of the individual. In some embodiments, an identifier may associate the at least second image with the biological sample and the at least one ridge and valley signature of the individual.

In another aspect, a system is provided for collection of a biological sample including a nucleic acid sample and at least one ridge and valley signature of an individual including: at least a first imaging component including a scanning surface configured to permit an energy wave to penetrate the scanning surface, where the energy wave is configured to image the at least one ridge and valley signature of an appendage of the individual; a substrate positioned upon the scanning surface; and where the substrate is configured to permit the collection of the at least one ridge and valley signature of the appendage through the substrate and to permit collection of the biological sample as the appendage is withdrawn from the substrate. In various embodiments, the system may be configured to collect the biological sample and collect the at least one ridge and valley signature are performed simultaneously.

In various embodiments, the scanning surface may be formed from a material selected from a plastic, a polyolefin, a polystyrene, a metal, a metal alloy, a glass, a silicon or combinations thereof. The material of the scanning surface may be transparent or translucent.

The system may further include a support for the substrate configured to permit the collection of the at least one ridge and valley signature through the support and the substrate. In various embodiments, the support may be formed from a material selected from a polymer, a metal, a metal alloy, a glass, a silicon material or combination thereof. The material of the support may be transparent or translucent.

In various embodiments, the substrate may be configured to be suitable for electrophoresis. In some embodiments, the substrate may be selected from a starch, an agarose, an alginate, a carrageenan or a synthetic polymer gel, or a mixture thereof.

In some embodiments, the substrate may be chemically modified with a chemical functional group selected from an amino group, a chloromethyl group, a hydroxyl group, a carboxyl group and a quaternary amino group. In other embodiments, the support may be chemically modified with a chemical functional group selected from an amino group, a chloromethyl group, a hydroxyl group, and a carboxyl group. In various embodiments, the chemical functional group modifying the substrate or support may include linkers selected from amino-functionalized linkers, sulfhydryl linkers, homobifunctional linkers and heterobifunctional linkers. In some embodiments, the substrate may be modified chemically to attach, covalently or noncovalently, a reagent, including but not limited to an enzyme, a binding partner, a surfactant, an anionic polymer or a zwitterionic species.

In various embodiments, the substrate may further include an identifier to associate the biological sample of the individual with the at least one ridge and valley signature of the individual, where the identifier is alphanumeric, graphical, magnetic, or electromagnetic. In various embodiments, the support may further include an identifier to associate the biological sample of the individual with the at least one ridge and valley signature of the individual, where the identifier is alphanumeric, graphical, magnetic, or electromagnetic.

In various embodiments, the substrate identifier and/or the support identifier may be a barcode.

In various embodiments, the substrate may be configured to permit the release of the at least one nucleic acid from the biological sample.

In various embodiments, the at least one nucleic acid of the biological sample may migrate to a cathode upon application of an electrical current.

In various embodiments, the at least first imaging component may be an optical scanner or a capacitance scanner. In various embodiments, the at least first imaging component is selected from a camera, an active pixel imager, a CMOS imager, an imager that images in multiple wavelengths, a CCD camera, a photo detector array, and a TFT imager. In some embodiments, the at least one ridge and valley signature may be collected electronically. In some embodiments, the optical scanner may include a LED, laser diode, incandescent light source, or a multispectral imager.

The system may further include a processor configured to transmit the ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control and any combination thereof.

In various embodiments, the substrate may be configured for archiving the biological sample or for shipping the sample to another location for testing. In various embodiments, the support may be configured for archiving the biological sample or for shipping the sample to another location for testing.

The system may further include at least a second imaging component for collecting at least a second image of the individual, selected from a facial image, an iris image, a retinal image or an ear image of the individual. In some embodiments, an identifier may further associate the at least second image of the individual with the biological sample and the at least one ridge and valley signature of the individual.

The system may further include one or more additional components selected from an amplification component, a purification component, a separation component or any combination thereof. The additional components may be configured to perform one or more of the following: obtain the at least one nucleic acid from the biological sample; purify the at least one nucleic acid before further amplification and analysis; amplify the at least one nucleic acid; separate the amplified at least one nucleic acid; and/or detect the amplified at least one nucleic acid.

In yet another aspect, a method is provided to collect a biological sample including at least one nucleic acid and at least one ridge and valley signature of an individual, including: providing at least a first imaging component including a scanning surface configured to permit an energy wave to penetrate the scanning surface, where the energy wave is configured to image the at least one ridge and valley signature of an appendage of the individual; providing a substrate positioned over the scanning surface, where the substrate is configured to collect the biological sample; and where the substrate is configured to permit the collection of the at least one ridge and valley signature through the substrate; positioning an appendage of the individual on the substrate; collecting the at least one ridge and valley signature from the appendage imaged by the energy wave; and withdrawing the appendage from the substrate, thereby collecting the biological sample. In some embodiments, the steps of collecting the biological sample and collecting the at least one ridge and valley signature may be performed simultaneously.

The method may further include the step of transmitting the ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier to associate the biological sample of the individual with the at least one ridge and valley signature of the individual, where the identifier is alphanumeric, graphical, magnetic, or electromagnetic. In various embodiments, the identifier may be a barcode.

The method may further include the step of subjecting the biological sample to at least one of a polymerase chain reaction, a DNA sequencing reaction, STR analysis, SNP analysis, or Indel analysis.

The method may further include the step of archiving the biological sample on the substrate.

In various embodiments, the at least first imaging component may be an optical scanner or a capacitance scanner. In various embodiments, the at least first imaging component may be selected from a camera, an active pixel imager, a CMOS imager, an imager that images in multiple wavelengths, a CCD camera, a photo detector array, and a TFT imager. In some embodiments, the optical scanner includes a LED, laser diode, incandescent light source, or a multispectral imager. In some embodiments, the at least one ridge and valley signature may be collected electronically.

In various embodiments, the scanning surface may be formed from a material selected from a plastic, a polyolefin, a polystyrene, a metal, a metal alloy, a glass, a silicon or combinations thereof. In some embodiments, the material of the scanning surface may be transparent or translucent.

In various embodiments, the support is formed from a material selected from a polymer, a metal, a metal alloy, a glass, a silicon material or combination thereof. The material of the support may be transparent or translucent.

In various embodiments, the substrate is selected from a starch, an agarose, an alginate, a carrageenan or a synthetic polymer gel, or a mixture thereof. In various embodiments, the substrate may be chemically modified with a chemical functional group selected from an amino group, a chloromethyl group, a hydroxyl group, a carboxyl group and a quaternary amino group. In some embodiments, the substrate is modified chemically to attach, covalently or noncovalently, a reagent, including but not limited to an enzyme, a binding partner, a surfactant, an anionic polymer or a zwitterionic species.

In various embodiments, the substrate may further include a support. In some embodiments, the support may be formed from a material selected from a polymer, a metal, a metal alloy, a glass, a silicon material or combination thereof. In some embodiments, the support may be chemically modified with a chemical functional group selected from an amino group, a chloromethyl group, a hydroxyl group, and a carboxyl group. In some embodiments, the chemical functional group modifying the substrate or support may include linkers selected from amino-functionalized linkers, sulfhydryl linkers, homobifunctional linkers and heterobifunctional linkers.

The method may further include the step of subjecting the biological sample to at least one of a polymerase chain reaction, a DNA sequencing reaction, STR analysis, SNP analysis, or Indel analysis. In some embodiments, the at least one nucleic acid of the collected biological sample is not isolated or purified before being subjected to at least one of a polymerase chain reaction, a DNA sequencing reaction, STR analysis, SNP analysis, or Indel analysis.

The method may also include the step of collecting at least a second image of the individual, selected from a facial image, an iris image, a retinal image or an ear image of the individual. In some embodiments, an identifier may associate the at least second image with the biological sample and the at least one ridge and valley signature of the individual.

In yet another aspect, a system is provided for collection of a biological sample including a nucleic acid sample and at least one ridge and valley signature of an individual including: at least a first imaging component including a scanning surface configured to permit an energy wave to penetrate the scanning surface, where the energy wave is configured to image the at least one ridge and valley signature of an appendage of the individual; a substrate configured to be suitable for electrophoresis is positioned upon the scanning surface; a support for the substrate; where the scanning surface is positioned under the support, and further where the substrate and the support are configured to permit the collection of the at least one ridge and valley signature through the substrate and the support and to permit collection of the biological sample as the appendage is withdrawn from the substrate. In various embodiments, the system may be configured to collect the biological sample and collect the at least one ridge and valley signature are performed simultaneously.

In various embodiments, the scanning surface may be formed from a material selected from a plastic, a polyolefin, a polystyrene, a metal, a metal alloy, a glass, a silicon or combinations thereof. The material of the scanning surface may be transparent or translucent.

In various embodiments, the at least first imaging component may be an optical scanner or a capacitance scanner. In various embodiments, the at least first imaging component may be selected from a camera, an active pixel imager, a CMOS imager, an imager that images in multiple wavelengths, a CCD camera, a photo detector array, and a TFT imager. In some embodiments, the at least one ridge and valley signature may be collected electronically. In some embodiments, the optical scanner may include a LED, laser diode, incandescent light source, or a multispectral imager.

The system may further include a support for the substrate configured to permit the collection of the at least one ridge and valley signature through the support and the substrate. In various embodiments, the support may be formed from a material selected from a polymer, a metal, a metal alloy, a glass, a silicon material or combination thereof. The material of the support may be transparent or translucent.

In various embodiments, the substrate is selected from a starch, an agarose, an alginate, a carrageenan or a synthetic polymer gel, or a mixture thereof. In some embodiments, the substrate may be chemically modified with a chemical functional group selected from an amino group, a chloromethyl group, a hydroxyl group, a carboxyl group and a quaternary amino group.

In some embodiments, the support may be chemically modified with a chemical functional group selected from an amino group, a chloromethyl group, a hydroxyl group, and a carboxyl group.

In some embodiments, the chemical functional group modifying the substrate may include linkers selected from amino-functionalized linkers, sulfhydryl linkers, homobifunctional linkers and heterobifunctional linkers. In some embodiments, the chemical functional group modifying the support includes linkers may be selected from amino-functionalized linkers, sulfhydryl linkers, homobifunctional linkers and heterobifunctional linkers.

In some embodiments, the substrate may be modified chemically to attach, covalently or noncovalently, a reagent, including but not limited to an enzyme, a binding partner, a surfactant, an anionic polymer or a zwitterionic species. In some embodiments, the support may be modified chemically to attach, covalently or noncovalently, a reagent, including but not limited to an enzyme, a binding partner, a surfactant, an anionic polymer or a zwitterionic species.

In various embodiments, the substrate or the support may further include an identifier to associate the biological sample of the individual with the at least one ridge and valley signature of the individual, where the identifier is alphanumeric, graphical, magnetic, or electromagnetic. In some embodiments, the identifier may be a barcode. In various embodiments, the substrate and the support may be configured for archiving the biological sample or for shipping the sample to another location for testing.

In various embodiments, the substrate may be configured to permit the release of the at least one nucleic acid from the biological sample.

In various embodiments, the at least one nucleic acid of the biological sample may migrate to a cathode upon application of an electrical current.

The system may further include a processor configured to transmit the ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control and any combination thereof.

In various embodiments, the substrate may be configured for archiving the biological sample or for shipping the sample to another location for testing. In various embodiments, the support may be configured for archiving the biological sample or for shipping the sample to another location for testing.

The system may further include at least a second imaging component for collecting at least a second image of the individual, selected from a facial image, an iris image, a retinal image or an ear image of the individual. In some embodiments, an identifier may further associate the at least second image of the individual with the biological sample and the at least one ridge and valley signature of the individual.

The system may further include one or more additional components selected from an amplification component, a purification component, a separation component or any combination thereof. The additional components may be configured to perform one or more of the following: obtain the at least one nucleic acid from the biological sample; purify the at least one nucleic acid before further amplification and analysis; amplify the at least one nucleic acid; separate the amplified at least one nucleic acid; and/or detect the amplified at least one nucleic acid.

In a further aspect, a method is provided to collect a biological sample including at least one nucleic acid sample and at least one ridge and valley signature of an individual, including the steps of: providing at least a first imaging component configured to provide an energy wave, where the at least a first imaging component includes a scanning surface configured to permit an energy wave to penetrate the scanning surface, where the energy wave is configured to image the at least one ridge and valley signature of an appendage of the individual; and providing a substrate configured to be suitable for electrophoresis upon the scanning surface; providing a support under the substrate, where the substrate and the support are configured to permit the collection of the at least one ridge and valley signature through the substrate and the support; collecting the at least one ridge and valley signature; and withdrawing the appendage from the scanning surface, thereby collecting the biological sample. In some embodiments, the steps of collecting the biological sample and collecting the at least one ridge and valley signature may be performed simultaneously. In some embodiments, the appendage may be a finger, toe, palm of a hand or sole of a foot.

The method may further include the step of transmitting the at least one ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier to associate the biological sample of the individual with the at least one ridge and valley signature of the individual, where the identifier is alphanumeric, graphical, magnetic, or electromagnetic. In various embodiments, the identifier may be a barcode.

The method may further include the step of subjecting the biological sample to at least one of a polymerase chain reaction, a DNA sequencing reaction, STR analysis, SNP analysis, or Indel analysis. In some embodiments, the at least one nucleic acid of the collected biological sample may not be isolated or purified before being subjected to at least one of a polymerase chain reaction, a DNA sequencing reaction, STR analysis, SNP analysis, or Indel analysis.

The method may further include the step of archiving the substrate containing the biological sample.

The method may also include the step of collecting at least a second image of the individual, selected from a facial image, an iris image, a retinal image or an ear image of the individual. In some embodiments, an identifier may associate the at least second image with the biological sample and the at least one ridge and valley signature of the individual.

In various embodiments, the at least first imaging component may be an optical scanner or a capacitance scanner. In various embodiments, the at least first imaging component may be selected from a camera, an active pixel imager, a CMOS imager, an imager that images in multiple wavelengths, a CCD camera, a photo detector array, and a TFT imager. In some embodiments, the at least one ridge and valley signature may be collected electronically. In some embodiments, the optical scanner may include a LED, laser diode, incandescent light source, or a multispectral imager.

In various embodiments, the scanning surface may be formed from a material selected from a plastic, a polyolefin, a polystyrene, a metal, a metal alloy, a glass, a silicon or combinations thereof. In some embodiments, the material of the scanning surface may be transparent or translucent.

In various embodiments, the substrate may include a gel. In various embodiments, the gel may be a starch, agarose, alginate, carrageenan or synthetic polymer gel, or a mixture thereof. In some embodiments, the gel may be configured to permit electrophoresis.

The method may further include the step of electrophoresing the biological sample on the gel to concentrate the at least one nucleic acid.

In various embodiments, the substrate may further include a support. In various embodiments, the support may be formed from a material selected from a polymer, a metal, a metal alloy, a glass, a silicon material or combination thereof. In some embodiments, the support may be transparent or translucent.

In another aspect, a system is provided for simultaneous collection of biological sample including a nucleic acid sample and at least one ridge and valley signature of an individual including: at least a first imaging component having a housing including a scanning surface configured to permit an energy wave to penetrate the scanning surface, where the energy wave is configured to image the at least one ridge and valley signature of an appendage of the individual; a substrate; a support for the substrate; a lysis solution incorporated onto or applied to the substrate; and where the substrate is configured to permit at least a portion of the appendage to contact the scanning surface to collect at least one ridge and valley signature and further where the substrate is configured to collect the biological sample as the appendage is withdrawn from the scanning surface. In some embodiments, the substrate accommodates four fingers. In some embodiments, the support is formed from a material selected from a polymer, a metal, a metal alloy, a glass, a silicon material or combination thereof.

In various embodiments, the scanning surface may be formed from a material selected from a plastic, a polyolefin, a polystyrene, a metal, a metal alloy, a glass, a silicon or combinations thereof. The material of the scanning surface may be transparent or translucent.

In various embodiments, the substrate may include a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof. In some embodiments, the paper material may further include a lysis solution. In various embodiments, the lysis solution includes proteinase K. In various embodiments, the lysis solution may include an enzyme selected from a serine protease, a cysteine protease, an acid protease, a metalloprotease, an aminopeptidase, a carboxypeptidase, a pancreatic proteolytic enzyme and a keratinase.

In various embodiments, the at least first imaging component may be an optical scanner or a capacitance scanner. In various embodiments, the at least first imaging component may be selected from a camera, an active pixel imager, a CMOS imager, an imager that images in multiple wavelengths, a CCD camera, a photo detector array, and a TFT imager. In some embodiments, the at least one ridge and valley signature may be collected electronically. In some embodiments, the optical scanner may include a LED, laser diode, incandescent light source, or a multispectral imager.

The system may further include a support for the substrate configured to permit the collection of the at least one ridge and valley signature through the support and the substrate. In various embodiments, the support may be formed from a material selected from a polymer, a metal, a metal alloy, a glass, a silicon material or combination thereof. The material of the support may be transparent or translucent.

The system may further include a processor configured to transmit the ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control and any combination thereof.

In various embodiments, the substrate may be configured for archiving the biological sample or for shipping the sample to another location for testing. In various embodiments, the support may be configured for archiving the biological sample or for shipping the sample to another location for testing.

The system may further include at least a second imaging component for collecting at least a second image of the individual, selected from a facial image, an iris image, a retinal image or an ear image of the individual. In some embodiments, an identifier may further associate the at least second image of the individual with the biological sample and the at least one ridge and valley signature of the individual.

The system may further include one or more additional components selected from an amplification component, a purification component, a separation component or any combination thereof. The additional components may be configured to perform one or more of the following: obtain the at least one nucleic acid from the biological sample; purify the at least one nucleic acid before further amplification and analysis; amplify the at least one nucleic acid; separate the amplified at least one nucleic acid; and/or detect the amplified at least one nucleic acid.

In yet another aspect, a method is provided for simultaneous collection of biological sample including a nucleic acid sample and at least one ridge and valley signature of an individual including: providing at least a first imaging component having a housing including a scanning surface configured to permit an energy wave to penetrate the scanning surface, where the energy wave is configured to image the at least one ridge and valley signature of an appendage of the individual; providing a substrate; providing a support for the substrate; providing a lysis solution configured to be incorporated onto the substrate or applied to the substrate; positioning an appendage of the individual on the substrate, where a portion of the appendage contacts the scanning surface; collecting the at least one ridge and valley signature from the appendage imaged by the energy wave; and withdrawing the appendage from the substrate, thereby collecting the biological sample on the substrate. In some embodiments, the substrate may accommodate four fingers.

The method may further include the step of transmitting the at least one ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier to associate the biological sample of the individual with the at least one ridge and valley signature of the individual, where the identifier is alphanumeric, graphical, magnetic, or electromagnetic. In various embodiments, the identifier may be a barcode.

The method may further include the step of subjecting the biological sample to at least one of a polymerase chain reaction, a DNA sequencing reaction, STR analysis, SNP analysis, or Indel analysis.

The method may further include the step of archiving the substrate containing the biological sample.

In various embodiments, the at least first imaging component may be an optical scanner or a capacitance scanner. In various embodiments, the at least first imaging component is selected from a camera, an active pixel imager, a CMOS imager, an imager that images in multiple wavelengths, a CCD camera, a photo detector array, and a TFT imager. In some embodiments, the at least one ridge and valley signature is collected electronically. In some embodiments, the optical scanner may include a LED, laser diode, incandescent light source, or a multispectral imager.

In various embodiments, the scanning surface may be formed from a material selected from a plastic, a polyolefin, a polystyrene, a metal, a metal alloy, a glass, a silicon or combinations thereof. In some embodiments, the material of the scanning surface may be transparent or translucent.

In various embodiments, the substrate may include a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof. In some embodiments, the paper material may further include a lysis solution. In various embodiments, the lysis solution may include proteinase K. In various embodiments, the lysis solution may include an enzyme selected from a serine protease, a cysteine protease, an acid protease, a metalloprotease, an aminopeptidase, a carboxypeptidase, a pancreatic proteolytic enzyme and a keratinase.

In various embodiments, the substrate further includes a support. In various embodiments, the support may be formed from a material selected from a polymer, a metal, a metal alloy, a glass, a silicon material or combination thereof. In some embodiments, the support may be transparent or translucent.

The method may further include the step of subjecting the biological sample to at least one of a polymerase chain reaction, a DNA sequencing reaction, STR analysis, SNP analysis, or Indel analysis. In some embodiments, the at least one nucleic acid of the collected biological sample may not be isolated or purified before being subjected to at least one of a polymerase chain reaction, a DNA sequencing reaction, STR analysis, SNP analysis, or Indel analysis.

The method may also include the step of collecting at least a second image of the individual, selected from a facial image, an iris image, a retinal image or an ear image of the individual. In some embodiments, an identifier associates the at least second image with the biological sample and the at least one ridge and valley signature of the individual.

In yet a further aspect, a system is provided for simultaneous collection of a biological sample including at least one nucleic acid sample and at least one ridge and valley signature of an individual, including: at least one imaging component including: a housing having a trough; a scanning surface below and in contact with the trough, where the scanning surface and trough are configured to permit an energy wave to penetrate the scanning surface and the trough, and to image the at least one ridge and valley signature of an appendage of the individual through the trough; the housing further includes a depression where the trough and the scanning surface reside; and a substrate positioned within the depression and in contact with and proximal to the trough, where the substrate is configured to collect the biological sample as the appendage is withdrawn from the scanning surface. In some embodiments, the trough may contain a lysis solution.

In various embodiments, the scanning surface may be formed from a material selected from a plastic, a polyolefin, a polystyrene, a metal, a metal alloy, a glass, a silicon or combinations thereof. The material of the scanning surface may be transparent or translucent.

In various embodiments, the substrate includes a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof. In some embodiments, the paper material may further include a lysis solution. In various embodiments, the lysis solution may include proteinase K. In various embodiments, the lysis solution may include an enzyme selected from a serine protease, a cysteine protease, an acid protease, a metalloprotease, an aminopeptidase, a carboxypeptidase, a pancreatic proteolytic enzyme and a keratinase.

In various embodiments, the at least first imaging component may be an optical scanner or a capacitance scanner.

In various embodiments, the at least first imaging component may be selected from a camera, an active pixel imager, a CMOS imager, an imager that images in multiple wavelengths, a CCD camera, a photo detector array, and a TFT imager. In some embodiments, the at least one ridge and valley signature may be collected electronically. In some embodiments, the optical scanner may include a LED, laser diode, incandescent light source, or a multispectral imager.

The system may further include a support for the substrate configured to permit the collection of the at least one ridge and valley signature through the support and the substrate. In various embodiments, the support may be formed from a material selected from a polymer, a metal, a metal alloy, a glass, a silicon material or combination thereof. The material of the support may be transparent or translucent.

In some embodiments, the substrate may include an identifier to associate the biological sample of the individual with the at least one ridge and valley signature of the individual, where the identifier is alphanumeric, graphical, magnetic, or electromagnetic. In some embodiments, the substrate identifier may be a barcode. In some embodiments, the support may include an identifier to associate the biological sample of the individual with the at least one ridge and valley signature of the individual, where the identifier is alphanumeric, graphical, magnetic, or electromagnetic. In some embodiments, the support identifier may be a barcode.

The system may further include a processor configured to transmit the ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control and any combination thereof.

In various embodiments, the substrate is configured for archiving the biological sample or for shipping the sample to another location for testing. In various embodiments, the support may be configured for archiving the biological sample or for shipping the sample to another location for testing.

The system may further include at least a second imaging component for collecting at least a second image of the individual, selected from a facial image, an iris image, a retinal image or an ear image of the individual. In some embodiments, an identifier may further associate the at least second image of the individual with the biological sample and the at least one ridge and valley signature of the individual.

The system may further include one or more additional components selected from an amplification component, a purification component, a separation component or any combination thereof. The additional components may be configured to perform one or more of the following: obtain the at least one nucleic acid from the biological sample; purify the at least one nucleic acid before further amplification and analysis; amplify the at least one nucleic acid; separate the amplified at least one nucleic acid; and/or detect the amplified at least one nucleic acid.

In another aspect, a system is provided for simultaneous collection of a biological sample including at least one nucleic acid sample and at least one ridge and valley signature of an individual including: at least one imaging component including: a housing having a trough; a recessed area configured to position a portion of an appendage of the individual having at least one ridge and valley signature positioned within the recessed area; a scanning surface within the recessed area where the scanning surface is configured to permit an energy wave to penetrate the scanning surface and the trough, where the energy wave is configured to image the at least one ridge and valley signature; and a substrate positioned in the trough; where the substrate is configured: to be suitable for electrophoresis; to permit the collection of the at least one ridge and valley signature through the substrate; and to permit the collection of the biological sample as the appendage is withdrawn from the substrate.

In various embodiments, the scanning surface may be formed from a material selected from a plastic, a polyolefin, a polystyrene, a metal, a metal alloy, a glass, a silicon or combinations thereof. The material of the scanning surface may be transparent or translucent.

The system may further include a support for the substrate configured to permit the collection of the at least one ridge and valley signature through the support and the substrate. In various embodiments, the support may be formed from a material selected from a polymer, a metal, a metal alloy, a glass, a silicon material or combination thereof. The material of the support may be transparent or translucent.

In various embodiments, the at least first imaging component may be an optical scanner or a capacitance scanner. In various embodiments, the at least first imaging component is selected from a camera, an active pixel imager, a CMOS imager, an imager that images in multiple wavelengths, a CCD camera, a photo detector array, and a TFT imager. In some embodiments, the at least one ridge and valley signature may be collected electronically. In some embodiments, the optical scanner may include a LED, laser diode, incandescent light source, or a multispectral imager.

In some embodiments, the substrate may include an identifier to associate the biological sample of the individual with the at least one ridge and valley signature of the individual, where the identifier is alphanumeric, graphical, magnetic, or electromagnetic. In some embodiments, the substrate identifier may be a barcode. In some embodiments, the support may include an identifier to associate the biological sample of the individual with the at least one ridge and valley signature of the individual, where the identifier is alphanumeric, graphical, magnetic, or electromagnetic. In some embodiments, the support identifier may be a barcode.

In various embodiments, the substrate may be selected from a starch, an agarose, an alginate, a carrageenan or a synthetic polymer gel, or a mixture thereof.

The system may further include an anode in electrical connection with a first edge of the substrate and a cathode in electrical connection with a second edge of the substrate.

The system may further include a processor configured to transmit the ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control and any combination thereof.

In various embodiments, the substrate may be configured for archiving the biological sample or for shipping the sample to another location for testing. In various embodiments, the support may be configured for archiving the biological sample or for shipping the sample to another location for testing.

The system may further include at least a second imaging component for collecting at least a second image of the individual, selected from a facial image, an iris image, a retinal image or an ear image of the individual. In some embodiments, an identifier may further associate the at least second image of the individual with the biological sample and the at least one ridge and valley signature of the individual.

The system may further include one or more additional components selected from an amplification component, a purification component, a separation component or any combination thereof. The additional components may be configured to perform one or more of the following: obtain the at least one nucleic acid from the biological sample; purify the at least one nucleic acid before further amplification and analysis; amplify the at least one nucleic acid; separate the amplified at least one nucleic acid; and/or detect the amplified at least one nucleic acid.

In yet a further aspect, a method is provided to capture a biological sample including at least one nucleic acid and at least one ridge and valley signature of an individual including the steps of: applying a lysis solution to a transparent substrate where the transparent substrate is positioned above a scanning surface configured to permit an energy wave to penetrate the scanning surface, and further where the energy wave is configured to image the at least one ridge and valley signature; placing a finger onto the transparent substrate; collecting the at least one ridge and valley signature of the finger through the transparent substrate; and collecting the biological sample including at least one nucleic acid from the transparent substrate.

In various embodiments, the transparent substrate may be selected from a starch, an agarose, an alginate, a carrageenan or a synthetic polymer gel, or a mixture thereof.

In various embodiments, the lysis solution may include proteinase K. In various embodiments, the lysis solution may include an enzyme selected from a serine protease, a cysteine protease, an acid protease, a metalloprotease, an aminopeptidase, a carboxypeptidase, a pancreatic proteolytic enzyme and a keratinase.

In some embodiments, the transparent substrate is chemically modified with a chemical functional group selected from an amino group, a chloromethyl group, a hydroxyl group, a carboxyl group and a quaternary amino group.

The method may further include the step of transmitting the at least one ridge and valley signature of the individual to at least one database including ridge and valley signatures selected from the group consisting of a forensic, criminal, identity, child identity, missing persons, immigration, department of motor vehicles, terrorist, paternity, arrestee, convict database, access control or any combination thereof.

The method may further include the step of providing an identifier to associate the biological sample of the individual with the at least one ridge and valley signature of the individual, where the identifier is alphanumeric, graphical, magnetic, or electromagnetic. In various embodiments, the identifier may be a barcode. In some embodiments, the transparent substrate may be provided with the identifier.

The method may further include the step of subjecting the biological sample to at least one of a polymerase chain reaction, a DNA sequencing reaction, STR analysis, SNP analysis, or Indel analysis.

In various embodiments, the at least first imaging component may be an optical scanner or a capacitance scanner. In various embodiments, the at least first imaging component may be selected from a camera, an active pixel imager, a CMOS imager, an imager that images in multiple wavelengths, a CCD camera, a photo detector array, and a TFT imager. In some embodiments, the at least one ridge and valley signature may be collected electronically. In some embodiments, the optical scanner may include a LED, laser diode, incandescent light source, or a multispectral imager.

In various embodiments, the scanning surface may be formed from a material selected from a plastic, a polyolefin, a polystyrene, a metal, a metal alloy, a glass, a silicon or combinations thereof. In some embodiments, the material of the scanning surface may be transparent or translucent.

The method may further include the step of subjecting the biological sample to at least one of a polymerase chain reaction, a DNA sequencing reaction, STR analysis, SNP analysis, or Indel analysis. In some embodiments, the at least one nucleic acid of the collected biological sample may not be isolated or purified before being subjected to at least one of a polymerase chain reaction, a DNA sequencing reaction, STR analysis, SNP analysis, or Indel analysis.

The method may also include the step of collecting at least a second image of the individual, selected from a facial image, an iris image, a retinal image or an ear image of the individual. In some embodiments, an identifier associates the at least second image with the biological sample and the at least one ridge and valley signature of the individual.

In some embodiments, at least one nucleic acid may be released from the finger and onto the transparent membrane.

The method may further include the step of archiving the substrate containing the biological sample. In some embodiments, the transparent substrate containing the at least one nucleic acid may be dried. In some embodiments, the dried transparent substrate containing the at least one nucleic acid may be used for genotyping analysis.

In yet another aspect a kit is provided including a substrate according to any one of the embodiments described above in the systems and methods provided herein, and, optionally, instructions.

In the following description, certain aspects and embodiments will become evident. It should be understood that a given embodiment need not have all aspects and features described herein. It should be understood that these aspects and embodiments are merely exemplary and explanatory and are not restrictive of the invention.

There still exists a need for improved systems, kits, and methods for collecting fingerprint, toe print, hand palm prints or foot sole prints and biological sample data for purposes of identifying and confirming the identity of a human individual.

BRIEF DESCRIPTION OF THE DRAWINGS

The skilled artisan will understand that the drawings described below are for illustration purposes only. The drawings are not intended to limit the scope of the present teachings in any way.

FIGS. 6A-6B illustrate a system having a housing, a trough and a substrate for collecting a ridge and valley signature and nucleic acid of an individual, in accordance with various embodiments.

DETAILED DESCRIPTION

Figure 1A:
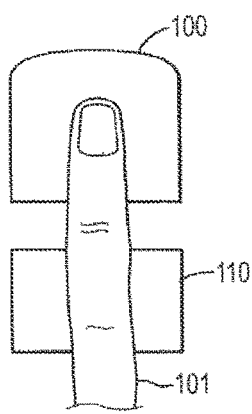
FIG. 1A illustrates a system for the simultaneous collection of the ridge and valley signature of a digit (a finger or toe print) and a biological sample from an individual, in accordance with various embodiments.

For the purposes of interpreting of this specification, the following definitions will apply and whenever appropriate, terms used in the singular will also include the plural and vice versa. In the event that any definition set forth below conflicts with the usage of that word in any other document, including any document incorporated herein by reference, the definition set forth below shall always control for purposes of interpreting this specification and its associated claims unless a contrary meaning is clearly intended (for example in the document where the term is originally used). It is noted that, as used in this specification and the appended claims, the singular forms "a," "an," and "the," include plural referents unless expressly and unequivocally limited to one referent. The use of "or" means "and/or" unless stated otherwise. The use of "comprise," "comprises," "comprising," "include," "includes," and "including" are interchangeable and not intended to be limiting. Furthermore, where the description of one or more embodiments uses the term "comprising," those skilled in the art would understand that, in some specific instances, the embodiment or embodiments can be alternatively described using the language "consisting essentially of" and/or "consisting of."

As used herein, "DNA" and "nucleic acid" are used interchangeably.

As used herein "oligonucleotide" and "polynucleotide" are interchangeable and generally refers to a polymer of nucleotide subunits having a fragment size of about or less than 200 base pairs.

As used herein, "biological sample" refers to a component originating from either within or on the body of an individual.

As used herein, "body fluid" refers to liquids originating within the body of an individual.

As used herein, "digital imaging apparatus" refers to an apparatus capable of digitizing an image of an object.

As used herein, "DNA sequencing" refers to the determination of the sequential identity of nucleotides in a molecule of DNA.

As used herein, "filter paper" refers to a semi-permeable paper.

As used herein, "a housing" refers to a structure surrounding at least in part an apparatus capable of performing a physical movement or carrying out a physical action including but not limited to illuminating, scanning and the like.

As used herein, "identifier" refers to a label capable of use in cataloging/correlating like-labeled data or data from a single source.

As used herein, "image capturing device" refers to a type of camera or scanning device.

As used herein, "imaging component" refers to an apparatus capable of performing at least one of capturing, developing, storing, retrieving and transmitting an image.

As used herein, "Indel" refers to an insertion or deletion of a segment of nucleic acid, usually DNA, within a nucleic acid sequence.

As used herein, "isolated" refers to separation of nucleic acid from either or both naturally occurring materials or environmental chemicals/substances.

As used herein, "light emitting diodes" refers to LEDs, a semiconductor light source.

As used herein, "microneedle" refers to a needle with a diameter less than 1 mm and penetration depth less than 3 mm.

As used herein, "multispectral illuminator" refers to a plurality of frequencies/wavelengths across the electromagnetic spectrum used to capture image data.

As used herein, "needle" refers to a hollow cylinder with a sharp point at one end. The needle may further comprise a beveled area in relation to the point or an absorbent material posterior to the pointed end, either located within the lumen or attached to the exterior of the cylinder.

As used herein, "optically collecting" refers to obtaining data, such as a ridge and valley signature or an image through illuminating the data or image and capturing the result.

As used herein, "digit" refers to one of several most distal parts of a limb, and includes a finger or toe.

As used herein, "photographic apparatus" refers to an LED camera, a digital camera, a still camera, a video camera and a virtual camera.

As used herein, "polymerase chain reaction" or PCR is a an amplification of nucleic acid consisting of an initial denaturation step which separates the strands of a double stranded nucleic acid sample, followed by repetition of (i) an annealing step, which allows amplification primers to anneal specifically to positions flanking a target sequence; (ii) an extension step which extends the primers in a 5' to 3' direction thereby forming an amplicon polynucleotide complementary to the target sequence, and (iii) a denaturation step which causes the separation of the amplicon from the target sequence (Mullis et al., eds, The Polymerase Chain Reaction, BirkHauser, Boston, Mass. (1994)). Each of the above steps may be conducted at a different temperature, preferably using an automated thermocycler (Applied Biosystems LLC, a division of Life Technologies Corporation, Foster City, Calif.). If desired, RNA samples can be converted to DNA/RNA heteroduplexes or to duplex cDNA by methods known to one of skill in the art. The PCR method also includes reverse transcriptase-PCR and other reactions that follow principles of PCR.

As used herein, "ridge and valley signature" refers to the friction ridges also known as surface contours on the palmar surface of the fingers, surface of the palm and hand and plantar surface of the feet and toes. In particular, the friction ridges provided by the impressions made from imaging one or more fingers are known as fingerprints.

As used herein, "SNP analysis" refers to the evaluation of the presence or absence of a single nucleotide polymorphism (SNP) marker following amplification of the locus containing the SNP marker As used herein, "STR analysis" refers to the evaluation of the alleles of a short tandem repeat (STR) marker following amplification of the locus containing the STR marker.

As used herein, "succession" refers to a sequence of steps performed.

As used herein, "substrate suitable for electrophoresis" refers to a matrix which can support the migration of species, including but not limited to nucleic acids when exposed to an electrical current such as electrophoresis.

As used herein, "topological impression" refers to the ridge and valley topography of a finger, palm, toe or foot.

As used herein, "withdrawing" or "withdrawn" refers to removing an appendage from the scanning surface while still exerting pressure upon the substrate. The resultant swiping motion assists in the collection of a biological sample on the substrate.

Reference will now be made to various embodiments, examples of which are illustrated in the accompanying drawings.

The present teachings relate to systems, kits, and methods for collecting at least one nucleic acid sample and at least one ridge and valley signature from an individual. A system according to the invention can find use in, but is not limited to, forensic, criminal, identity, child identity, missing persons, immigration, department of motor vehicles, terrorist, paternity, arrestee, access control or convict database applications. Furthermore, the ability to rapidly correlate the ridge and valley signature of an individual, such as a finger or toe print, palm or sole print with a nucleic acid profile, such as a DNA fingerprint, can provide rapid screening and identification of persons of nefarious intent, suspected of having conducted illegal activities, suspects in criminal investigations and persons of interest and can prevent access of such persons to situations where they might harm others, such as an airline flight, entrance into a high security access area or other sites where access is restricted or poses a security risk. Rapid correlation can also aid in identification and resolution of missing person investigations. In other applications, rapid correlation of nucleic acid profiles and a valley and ridge signature can be used in assisting proper familial identification in immigration and political asylum investigations.

System.

A system for collecting a biological sample comprising at least one nucleic acid sample and at least one ridge and valley signature of an individual includes at least one imaging component to image the at least one ridge and valley signature of the individual and a substrate configured to collect the biological sample comprising at least one nucleic acid from the individual.

The biological sample comprising at least one nucleic acid is collected from the skin of the appendage of the individual. The skin is a complicated organ and includes more than one layer of cell and tissue type. The epidermis refers to the tissues on the surface of human or animal skin and includes materials secreted therefrom or derived from the lower layers of the skin, from which DNA can be easily obtained for use in identifying the individual. The outermost layer of the skin is the stratum corneum. Below the epidermis layer of the skin is the dermis layer containing fibroblasts, macrophages and adipocytes, three cell types each having a nucleus containing nucleic acid. In addition the dermis has a vascular network of blood veins, arteries and lymph vessel containing white blood cells having a nucleus as does the erector pili muscle tissue, sebaceous glands and body fluids also present within the dermis. Additionally, sweat glands and vessels in the dermis may contain genetic materials in the form of intact cells or as free DNA, which may be released up to the epidermis for collection by the systems and methods of the invention. Any or all of these nucleic acid containing materials are encompassed by the biological sample. In various embodiments of the invention, collecting the biological sample is non-invasive.

The system may collect simultaneously at least one ridge and valley signature of an individual and a biological sample comprising nucleic acid or may collect in succession the signature and biological sample or, visa versa, the biological sample and the signature with an at least first imaging component. The methods of collection provide collection of both the biological sample and the at least one ridge and valley signature while the individual may touch only one apparatus. Additional motions or steps of touching additional platens or substrates may not be required to collect the biological sample and the at least one ridge and valley signature. The ridge refers to a friction ridge, the raised part of the epidermal layer of the skin of the fingers, toes, palm of the hand or sole of the foot and the valley being the depression in the epidermis between two adjacent ridges. The ridges and valleys are commonly referred to as fingerprints, palm prints, toe prints or footprints depending on the origin of the ridge and valley signature.

At Least a First Imaging Component.

In various embodiments, the system includes at least a first imaging component configured to obtain a ridge and valley signature of the individual. The imaging component may employ energy waves, such as light as described above, or other energy waves such as electromagnetic waves, capacitance, infra-red or sonic, e.g., ultrasound based components to provide an image of the ridge and valley signature. When the term imaging component is used in the context of capturing ridge and valley signatures, this includes any component that captures a digital or analog electronic representation of ridge and valley signatures.

Ridge and valley signatures may also be obtained using a touchless three-dimensional ridge and valley scanner using a digital processing means. (Wang, Yongchang; Q. Hao, A. Fatehpuria, D. L. Lau and L. G. Hassebrook (2009). "Data Acquisition and Quality Analysis of 3-Dimensional Fingerprints". Florida: IEEE conference on Biometrics, Identity and Security. http://vis.uky.edu/~realtime3d/Doc/3D_Fingerprint_Quality.pdf. Retrieved March 2010. Wang, Yongchang; D. L. Lau and L. G. Hassebrook (2010). "Fitsphere unwrapping and performance analysis of 3D Fingerprints". Applied Optics. pp. 592-600.

In one embodiment of the present teachings, the system may include at least a first optical imaging component. In other embodiments, the system can include at least a first solid-state ridge and valley signature reader. The optical imaging component has an illuminating means for optically collecting the ridge and valley signature using an optical scanner as is known to one of skill in the art. The optical scanner can be an array of a plurality of light emitting diodes or a multispectral illuminator. The optical scanner may be a camera, an active pixel imager, a CMOS imager, an imager that images in multiple wavelengths, a CCD camera, a photo detector array, or a TFT imager. In an optical scanner a beam of light passes through scanning surface to illuminate the topological impression made by the appendage, including a finger, hand, palm, toe, sole or foot, when positioned against the scanning surface of the at least first imaging component.

Any suitable instrumentation may be used to acquire the image of an appendage according to the methods described herein. Some instruments and techniques include but are not limited to those disclosed in U.S. Pat. No. 4,537,484, U.S. Pat. No. 6,175,407, U.S. Pat. No. 6,665,427, U.S. Pat. No. 8,014,581, U.S. Pat. No. 8,036,431, U.S. Pat. No. 5,177,353, U.S. Pat. No. 6,282,303, U.S. Pat. No. 6,188,781, U.S. Pat. No. 6,741,729, U.S. Pat. No. 6,122,394, U.S. Pat. No. 6,826,000, U.S. Pat. No. 6,496,630, U.S. Pat. No. 6,628,813, U.S. Pat. No. 6,983,062, U.S. Pat. No. 7,162,060, U.S. Pat. No. 7,164,440, U.S. Pat. No. 7,657,067, U.S. Pat. No. 8,073,209, U.S. Pat. No. 7,190,817, U.S. Pat. No. 7,558,410, U.S. Pat. No. 7,565,541, U.S. Pat. No. 7,995,808, U.S. Pat. No. 7,899,217, U.S. Pat. No. 7,890,158, U.S. Pat. No. 7,835,554, U.S. Pat. No. 7,831,072, U.S. Pat. No. 7,819,311, U.S. Pat. No. 7,804,984, U.S. Pat. No. 7,801,339, U.S. Pat. No. 7,801,338, U.S. Pat. No. 7,751,594, U.S. Pat. No. 7,735,729, U.S. Pat. No. 7,668,350, U.S. Pat. No. 7,627,151, U.S. Pat. No. 7,620,212, U.S. Pat. No. 7,613,504, U.S. Pat. No. 7,545,963, U.S. Pat. No. 7,539,330, U.S. Pat. No. 7,508,965, U.S. Pat. No. 7,460,696, U.S. Pat. No. 7,440,597, U.S. Pat. No. 7,394,919, U.S. Pat. No. 7,386,152, U.S. Pat. No. 7,347,365, U.S. Pat. No. 7,263,213, U.S. Pat. No. 7,203,345, U.S. Pat. No. 7,147,153, U.S. Pat. No. 6,816,605, U.S. Pat. No. 6,628,809, U.S. Pat. No. 6,560,352, US20110235872, US20110211055, US20110165911, US20110163163, US20110085708, US20100246902, US20100067748, US20090245591, US20090148005, US20090092290, US20090080709, US20090046903, US20080304712, US20080298649, US20080297788, US20080232653, US20080192988, US20080025580, US20080025579, US20070116331, US20070030475, US20060274921, US20060244947, US20060210120, US20060202028, US20060110015, US20060062438, US20060002598, US20060002597, US20050271258, US20050265586, US20050265585, US20050205667, US20050185847, US20050007582, US20040240712, US20040047493, US20030223621, US20030078504, US20020183624, or US20020009213.

Scanning Surface.

The at least first imaging component comprises a scanning surface configured to permit the energy wave to penetrate the scanning surface, to image the at least one ridge and valley signature of an appendage of the individual positioned on at least a portion of the scanning surface. The scanning surface may be transparent or translucent to the energy wave used to image the at least one ridge and valley signature The scanning surface may be formed from a material selected from a plastic, a polyolefin, a polystyrene, a metal, a metal alloy, a glass, a silicon or combinations thereof. In some embodiments, the surface comprises derivatized plastic, derivatized polyolefin, derivatized polystyrene, derivatized metal, derivatized metal ally, derivatized glass, derivatized silicon or combination of materials.

Substrate.

The system provides a substrate configured to collect the biological sample from an appendage of the individual; wherein the scanning surface and the substrate are configured to permit collecting the at least one ridge and valley signature of the appendage while withdrawing the appendage from the substrate. In other embodiments, the system may be configured to collect at least one ridge and valley signature as a biological sample is collected from the appendage by exposure to a lysis solution. The system may provide non-invasive collection of the biological sample The substrate may be formed from materials that assist in collecting the biological sample comprising at least one nucleic acid. The substrate can be a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof.

In some embodiments, the substrate may be an anion exchange membrane. (e.g., AMI-7001, available from Membranes International Inc., Ringwood, N.J.) In one non-limiting example, the anion exchange membrane may be made of polystyrene/divinyl benzene copolymers that have been functionalized with quaternary amine groups. The functionalized membrane attracts nucleic acids contained in the biological sample. In other embodiments, an ion exchange membrane (Pall Corporation, Ann Arbor, Mich.) can be used for capturing nucleic acid.

In some embodiments, the system is configured to vibrate the paper or membrane material as the appendage is withdrawn.

In some embodiments, the substrate may further have microneedles impregnated within the substrate. Microneedles can abrade or otherwise scrape the skin of an appendage with or without vibration to increase the amount of skin cells, body fluid and nucleic acid that can be deposited onto the substrate.

In certain embodiments the use of an anion exchange or cation exchange membrane, or more generally an ion exchange membrane, for capturing nucleic acid may operate in the presence of a lysis solution. Basically, the nucleic acid is separated from a skin surface, including but not limited to a finger, to the positively charged quaternary amine groups of the membrane by displacing chloride ions. Following extraction of the nucleic acid, the membrane would be dried and a 0.8 to 1.5 mm punch taken for genotyping analysis.

In another embodiment, the substrate can contain about 10 uL to about 20 uL, a few drops (more than 20 uL, the equivalent of one drop), or be saturated with a lysis solution.

Figure 3A:
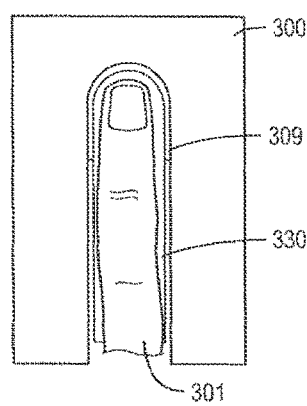
FIGS. 3A-3B are illustrations of a system in top view and in cross-section for collecting a ridge and valley signature and nucleic acid of an individual, in accordance with various embodiments.
Figure 3B:
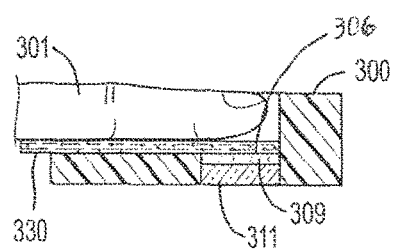

In other embodiments, the lysis solution may be the substrate. A lysis solution can form a film on a scanning surface of an imaging component having a depression or be present within a support positioned upon the scanning surface where the support contains a depression. In FIG. 3A finger 301 rests on a film of lysis solution 330 within a depression (not labeled). Lysis solution 330 can also cover the scanning surface 309 resting on support 311 as illustrated in FIG. 3B.

In some embodiments of the present teachings, the lysis solution may contain an enzyme to facilitate collection of DNA onto a substrate. In certain embodiments, the lysis solution contains proteinase K. In various embodiments, proteinase K may be present in the lysis solution at about 0.8 mg/ml to about 1.5 mg/ml. In certain other embodiments the lysis solution can contain a protease enzyme. The enzyme may degrade structural proteins in order to permit extraction of nucleic acids from live cells in the epidermis or dermis upon exposure of an area of a finger or hand. The enzyme may be applied to a substrate that is placed in contact with the subject's finger or hand, or the enzyme may be incorporated into the substrate, such as incorporation into a gel, film, or paper. In certain embodiments herein, the lysis solution comprises a polypeptide having protease activity such as for example, proteinase K.

In lieu of, or in addition to, proteinase K, the lysis solution can comprise a serine protease such as trypsin, chymotrypsin, elastase, subtilisin, streptogrisin, thermitase, aqualysin, plasmin, cucumisin, or carboxypeptidase A, D, C, or Y; a cysteine protease such as papain, calpain, or clostripain; an acid protease such as pepsin, chymosin, or cathepsin; or a metalloprotease such as pronase, thermolysin, collagenase, dispase, an aminopeptidase or carboxypeptidase A, B, E/H, M, T, or U. Qiagen Protease (p/n 19155, Qiagen, Valencia, Calif.) is an alternative to proteinase K and can be inactivated by EDTA.

In other embodiments, the enzyme contained in the lysis solution is a pancreatic proteolytic enzyme, such as porcine pancreatic enzyme. Keratinases, that may have utility in collection of nucleic acids, include but are not limited to keratinases isolated from bacteria or fungi. Some keratinases have enhanced stabilities in the presence of detergents, surfactant, metal ions and solvents, which is useful for the methods of the present teachings. Some nonlimiting examples of a keratinase useful in the methods of the present teachings include the keratinases from *P. pastoris, B. megaterium*, and *B. licheniformis*.

In other embodiments, the lysis solution may include a surfactant to assist collection of the biological sample from the appendage or to assist in extracting the at least one nucleic acid from the biological sample once collected. As used here, the term "detergent" is any substance that reduces the surface tension of water, and is used synonymously with the term "surfactant". In certain embodiments, the detergent can be a cationic detergent, anionic detergent, nonionic detergent, or a zwitterionic detergent. Examples of nonionic detergents include triton, such as the Triton™ X series (Triton™ X-100 t-Oct-$C_6H_4$-$(OCH2-CH_2)_x$OH, x=9-10, Triton™ X-100R, Triton™ X-114 x=7-8), octyl glucoside, polyoxyethylene(9)dodecyl ether, digitonin, IGEPAL™ CA630 octylphenyl polyethylene glycol, n-octyl-beta-D-glucopyranoside (betaOG), n-dodecyl-beta, Tween™ 20 polyethylene glycol sorbitan monolaurate, Tween™ 80 polyethylene glycol sorbitan monooleate, polidocanol, n-dodecyl beta-D-maltoside (DDM), NP-40 nonylphenyl polyethylene glycol, C12E8 (octaethylene glycol n-dodecyl monoether), hexaethyleneglycol mono-n-tetradecyl ether (C14EO6), octyl-beta-thioglucopyranoside (octyl thioglucoside, OTG), Emulgen, and polyoxyethylene 10 lauryl ether (C12E10). Examples of ionic detergents (anionic or cationic) include deoxycholate, sodium dodecyl sulfate (SDS), N-lauroylsarcosine, and cetyltrimethylammoniumbromide (CTAB). A zwitterionic reagent may also be used in the purification schemes of the present invention, such as Chaps, zwitterion 3-14, and 3-[(3-cholamidopropyl)dimethylammonio]-1-propanesulf-onate. It is contemplated also that urea may be added with or without another detergent or surfactant.

In some embodiments, a surfactant that substantially lacks fluorescence between 300 nm and 750 nm is used in the methods of the present teachings. In some embodiments provided herein, the lysis solution comprises a surfactant at a concentration that has low or no emission at the emission wavelengths of dyes or labels commonly used for detecting RNA or DNA when in use for in situ analysis of DNA, RNA or a surrogate thereof.

In some embodiments, an effective concentration of surfactant in a lysis mixture is a concentration of surfactant at which a sample is considered fully lysed as determined by propidium iodide staining using 1% TRITON X-100™ surfactant as a control. Lysis-effective concentrations of exemplary surfactants range from 0.02% or 0.05%, to 3% or more for TRITON X-114™ surfactant, from 0.1% to 5% or more for NP-40™ surfactant, and from 0.05% to 1% or to 3% for TRITON X-100™ surfactant. When a combination of surfactants is used, the concentration of each surfactant may be lowered from the cited amounts.

In various embodiments, the substrate may comprise a gel to collect the DNA sample from the appendage. In some embodiments, gels may be dimensionally stable enough to maintain structural integrity upon the scanning surface. In other embodiments, gels may be attached upon or to a support. In other embodiments, a gel substrate is in a fluid state within a support. Useful gels include but are not limited to starch, agarose, alginate, carrageenan or synthetic polymer gel, or a mixture thereof. The synthetic polymer may be a homopolymer or a copolymer, and/or may include a plurality of synthetic polymers. Agarose gels for electrophoresis are made between 0.7% and 2%. A 0.7% gel provides good separation (resolution) of large DNA fragments (5-10 kb) and a 2% gel will show good resolution for small fragments (0.2-1 kb). A 3% gel can be used for separating fragments less than 200 bp though a vertical polyacrylamide gel may also be used. Polyacrylamide gels may comprise one or more polymers or may comprise more than one type of acrylamide monomer within a polyacrylamide gel.

To form the gels that may be used as a substrate, all types of polymerization, including cationic, anionic, copolymerization, chain copolymerization, cross-linking, uncrosslinked polymerization, and the like can be employed to synthesize the polymer gels forming part or all of the substrate. Essentially any type of polymer or copolymer formable from a fluid precursor, including but not limited to homopolymers, random copolymers, terblock polymers, radial polymers, linear polymers, branched polymers, and graft copolymers, can be incorporated onto the support as part of all of the substrate. An exemplary, non-limiting list of polymers that are suitable include cellulose polymers, including but not limited to hydroxyethylcellulose (HEC), hydroxypropyl methylcellulose (HPMC), hydroxypropyl cellulose (HPC); derivatives of sugars including but not limited to dextrans, mannitols, and gluco-pyranosides; pluronic copolymer liquid crystals; polyurethane; polyacids, including but not limited to lactic acids, and acrylic acids; polyamides; polyacrylamides, including but not limited to unsubstituted, N-substituted, and N, N-disubstituted acrylamides; polycarbonates; polyacetylenes; polydiacetylenes; polyphosphazenes; polysiloxane; polyolefins; polyesters; polyethers; poly(ether ketones); poly(alkylene oxides, including but not limited to polyethyleneoxides (PEO), polyethylethylene glycols (PEG) and polypropylene oxides (PPO); poly(ethylene terephthalate); poly(methyl methacrylate); polystyrene; substituted polystyrene, including but not limited to polystyrene sulfonates (PSS) and polyanetholes (PASA); poly(vinylpyrrolidones; proteinaceous material, and/or combinations and/or copolymers of the above.

In some embodiments, the gel may be modified with chemically reactive groups to permit ionic, covalent or hydrogen bond interactions with species present within the biological sample. Suitable chemically reactive groups that may modify gels include but are not limited to thiols, amines, carboxylic acids or the like, as is generally known in the art. Some examples of chemical modifications include, but are not limited to, amino groups including aliphatic and aromatic amines, carboxylic acids, aldehydes, amides, chloromethyl groups, hydrazide, hydroxyl groups, sulfonates and phosphates. These functional groups can be used to add any number of modifications to the gel, generally using known chemistries, including, but not limited to the use of amino-functionalized linkers, sulfhydryl linkers, etc. There are a number of sulfhydryl reactive linkers known in the art such as SPDP, maleimides, alpha-haloacetyls, and pyridyl disulfides. Similarly, amino groups on the gel can be attached using linkers; for example, a large number of stable bifunctional groups are well known in the art, including homobifunctional and heterobifunctional linkers. In an additional embodiment, carboxyl groups on the gel can be derivatized using well-known linkers. For example, carbodiimides activate carboxyl groups for attack by good nucleophiles such as amines.

In some embodiments, the chemical modification of the gel substrate is performed to attach, covalently or noncovalently, a reagent, including but not limited to an enzyme, a binding partner, a surfactant, an anionic polymer or a zwitterionic species to assist in the collection of DNA from the subject. In some embodiments of the invention, a support such as a glass slide or plastic sheet may be modified covalently to attach a polymeric substrate layer upon the support, thus incorporating one or more of the chemical modifications described above. In other embodiments, a polymeric layer forming a substrate is formed on the support without covalent attachment to the support.

In yet other embodiments, when a substrate provided as a gel is modified chemically to covalently attach one or more reagents, an enzyme, including but not limited to proteinase K may be attached to the gel substrate to assist in extracting nucleic acids from the appendage or from the biological sample once collected. In other embodiments, an enzyme is covalently attached to the gel substrate, and may be a proteinase selected from the group consisting of keratinase, papain, bromelain, and proteinase K. In other embodiments, the gel substrate is modified covalently to attach an anionic polymer to assist in extracting nucleic acids from the appendage or from the biological sample once collected. In yet other embodiments, a surfactant is associated with the gel substrate noncovalently to assist in extracting nucleic acids from the appendage or from the biological sample once collected. In some embodiments, a zwitterionic species may be present in the gel substrate to assist in separating nucleic acids from other components of the cells collected. In some other embodiments, the gel substrate is chemically modified to covalently attach an antibody to a target moiety present on the skin of the appendage or in the collected biological sample, thus providing a binding partner to the target moiety. In some embodiments, wherein a binding partner is immobilized on the gel, cleavage of the binding partner along with or separately from its binding target moiety may be performed.

In certain embodiments, the gel substrate may have a lysis solution as the fluid in which the polymer is dissolved. In certain such embodiments, the lysis solution acts to extract nucleic acid from the skin in contact with the gel substrate.

In other embodiments, the gel, and optionally its support, is selected to be suitable for use under electrophoretic field conditions. In some embodiments, after withdrawal of the finger from the gel substrate, an electrical current can be applied to the gel substrate causing the at least one nucleic acid of the biological sample, which is negatively charged, to migrate towards the cathode when the gel substrate is operatively attached to an electrophoresis apparatus. The nucleic acid may become concentrated to a smaller region of the gel substrate and also isolated from cellular debris and environmental contaminants that may be contained in the biological sample collected from the skin. The concentrated sample in the smaller region of the gel substrate may be conveniently used for further genotyping analysis but also can provide a long term storage or archiving medium.

Support.

The system also may provide a support for the substrate. In some embodiments, the support may be configured to permit the collection of the at least one ridge and valley signature through the support or through the support and the substrate.

The support may be made of any material capable of forming a solid base. A suitable material for a support may have any of a variety of properties depending upon the particular embodiments, including for example, porous, nonporous, rigid, elastic, pliable, malleable, low temperature melting, high temperature melting, and/or chemically resistant to one or more solvents commonly used in the reactions set forth herein. In some embodiments, the support is formed from a material selected from a polymer, a metal, a metal alloy, a glass, a silicon material or combinations thereof. Suitable polymers include but are not limited to, plastic; polypropylene, polyethylene, polybutylene, polyurethane, nylon, polymer such as acrylic, acrylonitrile butadiene styrene (ABS), ULTEM (Polyetherimide), acetal copolymer, PROPYLUX HS (heat stabilized polypropylene), RADEL A (polyethersulfone), RADEL R (polyarylethersulfone), UDEL (polysulfone), NORYL PPO (polyphenylene oxide & styrene), Polycarbonate, UHMW-PE (ultra high molecular weight polyethylene), Polyetheretherketone (PEEK), polyphenylene sulfide (PPS, TECHTRON or RYTON), polyolefin or polystyrene; metal such as aluminum, iron, steel or an alloy; other materials such as glass or silicon, or derivatives or combinations of these or other suitable materials. In some of the embodiments of the present teachings, the support is made of a material that is transparent or translucent.

In some embodiments, the support is modified with chemically reactive groups to attach a substrate via ionic, covalent or hydrogen bonds. Chemically reactive groups include, but are not limited to thiols, amines, carboxylic acids, and the like. Some examples of chemical modifications include, but are not limited to, amino groups including aliphatic and aromatic amines, carboxylic acids, aldehydes, amides, chloromethyl groups, hydrazide, hydroxyl groups, sulfonates and phosphates. These functional groups can be used to add any number of modifications to the support, generally using known chemistries, including, but not limited to the use of amino-functionalized linkers, sulfhydryl linkers, etc. There are a number of sulfhydryl reactive linkers known in the art such as SPDP, maleimides, alpha-haloacetyls, and pyridyl disulfides. Similarly, amino groups on the support can be attached using linkers; for example, a large number of stable bifunctional groups are well known in the art, including homobifunctional and heterobifunctional linkers. In an additional embodiment, carboxyl groups present on the support can be derivatized using well-known linkers. For example, carbodiimides activate carboxyl groups for attack by good nucleophiles such as amines.

In some embodiments, the support is modified chemically to attach, covalently or noncovalently, a reagent, including but not limited to an enzyme, a binding partner, a surfactant, an anionic polymer or a zwitterionic species to assist in the collection of DNA from the subject. In some embodiments of the invention, a support such as a glass slide or plastic sheet may be modified covalently to attach a polymeric layer upon the support, thus incorporating one or more of the chemical modifications described above. In other embodiments, a polymeric layer forming a substrate is formed on the support without covalent attachment to the support.

The support may be formed to underlay the entire substrate, underlay part of the substrate or be attached to the substrate. The support may be formed to hold a liquid or non-rigid gel. It may be formed to fit around one or more fingers of a hand. The support may be formed to fit into a depression upon the scanning surface of the at least one imaging component.

In some embodiments, a support may contain a gel that can maintain its shape, a non-rigid gel or a liquid. The liquid contained in a support may include a lysis buffer, which may have additional chemical components added to it, as described above for the substrate from which the biological sample is collected.

Substrate Configurations.

The system provides for the substrate to be positioned in various configurations, in relationship to the scanning surface and, optionally, a support. In some embodiments, the substrate is positioned proximal to the scanning surface. In some embodiments, when the substrate is positioned proximal to the scanning surface, it is positioned upon or placed within a support. In other embodiments, a support is attached to the substrate; and at least a portion of the support is positioned over the scanning surface where the support is transparent or translucent. In other embodiments, the substrate is positioned on the support and the substrate and the support are positioned upon the scanning surface, where the support and the substrate are each translucent or transparent. In some embodiments, the transparent support may be attached to the substrate, wherein at least a portion of the transparent support is positioned over the scanning surface and at least a portion of the substrate is positioned proximal to the substrate. In other embodiments, the support is transparent or translucent and is attached to the substrate, wherein the support is configured to permit the collection of the at least one ridge and valley signature through the support, wherein the appendage is in direct contact with substrate and the support and operational contact with the scanning surface, thereby permitting collection of the at least one ridge and valley signature through the support, and further permitting collection of the biological sample as the appendage is withdrawn.

Additional Imaging Components.

In another embodiment of the present teachings, the system can further comprise at least a second imaging component for collecting a second image of the individual. The second image of the individual can be either the face of the individual or a component of the individual amenable to biometric identification. Suitable biometric images that may be collected as the second image include a retinal scan, or iris scan, the contours of the ear, facial recognition, hand geometry, foot geometry, voice, odor and scent.

Various exemplary embodiments of the system and methods of use are described herein, but the invention is not limited by the particular embodiments. In any of these embodiments, substrate with or without supports may be processed immediately in a further analysis or reaction, archived for future use, or shipped to another facility for processing or analysis. The image of the at least one ridge and valley signature may be sent to a database having a plurality of ridge and valley signatures as well as other physical biometric data. Each of the substrate, support and at least one ridge and valley signature may have an identifier assigned in order to associate the collected biological sample and the at least one ridge and valley signature with the individual.

FIG. 1A illustrates a system and method for simultaneous collection of a nucleic acid sample and a ridge and valley signature. The scanning surface 100 includes an imaging system that illuminates the ridge and valley signature of the finger 101 in contact with a substrate 110 and as the appendage is withdrawn, a biological sample, including but not limited to cells and extracellular nucleic acids from the epidermis and dermis layers of skin is deposited to the substrate 110. Substrate 110 can vibrate to encourage deposition of the biological sample.

Figure 1B:
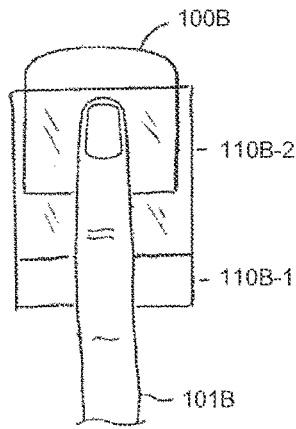
FIG. 1B illustrates a substrate for use in various embodiments of the invention.

A different arrangement and method is demonstrated with the substrate illustrated in FIG. 1B. In this embodiment, the substrate 110B-1 is attached to a support 110B-2. The substrate may be any suitable material, and may include any of paper, membrane, gel material, or any combination thereof. The support is transparent or translucent, permitting positioning of the support upon the scanning surface 100B. The attached substrate is positioned to not obscure the region of the scanning surface required to image the ridge and valley signature. An appendage 101B may be positioned on the combination substrate/support to permit imaging of the at least one ridge and valley signature through the support. As the imaging is collected, the appendage is withdrawn from the support/substrate. As the appendage is fully withdrawn, the biological sample including at least one nucleic acid is collected on substrate 110B-1.

Figure 2:
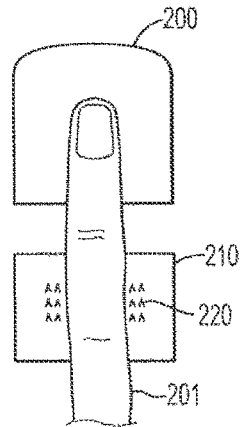
FIG. 2 illustrates a system for the simultaneous collection of the ridge and valley signature of a digit (a finger or toe print) and a biological sample from an individual by dragging a digit over or vibrating micro needles in contact with the digit, in accordance with various embodiments.

In another variation, the substrate 210 of FIG. 2 can have microneedles 220 impregnated within substrate 210. Microneedles 220 can abrade or otherwise scrape the skin of finger 201 with or without vibration to increase the amount of skin cells, body fluid and nucleic acid that can be deposited onto substrate 210, as the at least one ridge and valley signature collected and the biological sample is collected as the appendage is withdrawn from the substrate.

In certain embodiments the use of an anion exchange or ion exchange membrane for capturing nucleic acid would operate in the presence of a lysis solution, within the substrate as described above. The substrate can contain about 10 uL to about 20 uL, a few drops (more than 20 uL, the equivalent of one drop), or be saturated with a lysis solution. The substrate may be configured as in FIG. 1A, FIG. 1B, and FIG. 2. After collecting the at least one ridge and valley signature and withdrawing the appendage from the substrate to collect the biological sample including at least one nucleic acid, the membrane may be dried and a 0.8 to 1.5 mm punch taken for genotyping analysis.

In other embodiments a lysis solution can form a liquid film substrate on a scanning surface of an imaging component having a depression. In FIG. 3A finger 301 rests on a liquid film of lysis solution 330 within a depression (not labeled) of imaging component 300. Lysis solution 330 can also cover the scanning surface 309 resting on support 311 as illustrated in FIG. 3B. In other embodiments, the lysis solution may contain proteinase K, or other proteinases as described above. The ridge and valley signature may be collected as the finger rests within the imaging component, and the biological sample collected within the lysis solution during the image collection may be retrieved after the finger is removed from the system.

In other embodiments, as shown in FIG. 3B, scanner mechanism 311 for scanner element 309 provides the necessary electronics to convert the image that scanner 309 obtains into a digitized electronic form of the ridge and valley signature. The electronic ridge and valley signature may be stored locally, or communicated to a remote database for storage or other processing.

Figure 4A:
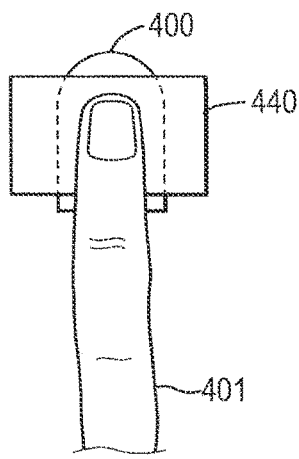
FIGS. 4A-4C contain illustrations of a substrate capable of electrophoresis for collecting a ridge and valley signature and nucleic acid of an individual, in accordance with various embodiments.
Figure 4B:
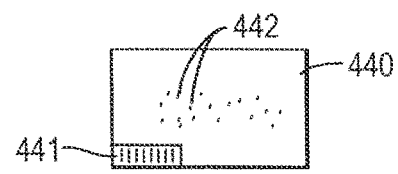

In certain embodiments, and as illustrated in FIG. 4A, a finger 401 rests on substrate 440 positioned above a scanning surface 400 for the collection of a nucleic acid sample and a ridge and valley signature. In certain such embodiments, the substrate 440 can be rigid gel. In some embodiments, the gel rests on a support, which may be a glass slide or other suitable material that is transparent or translucent. In some embodiments, the support may have an identifier 441, as shown in FIG. 4B.

In certain embodiments, the substrate 440, a gel, can have a lysis solution as the fluid in which the polymer is dissolved. In certain such embodiments, the lysis solution acts to extract nucleic acid from the skin in contact with the gel substrate 440.

Figure 4C:
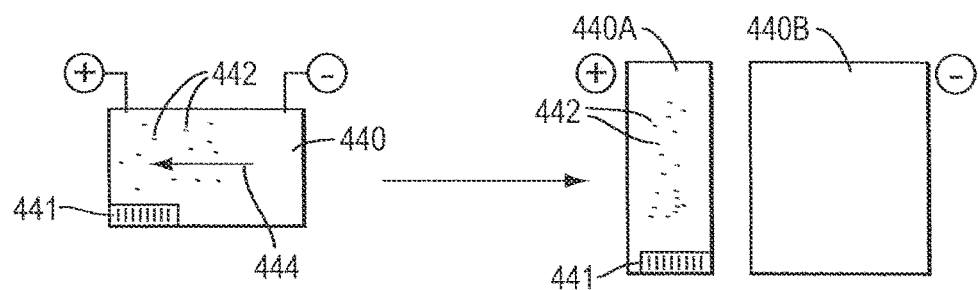

In some embodiments, the substrate 440 may be a substrate suitable for electrophoresis, as shown in FIG. 4C. After withdrawal of the finger 401 from the substrate 440 of FIG. 4A, an electrical current 444 can be applied to substrate 440 causing nucleic acid 442, which is negatively charged to migrate towards the cathode when substrate 440 is exposed to an electrophoresis apparatus (not shown). The nucleic acid 442 is driven under the electric field into substrate 440A, but is also separated from cellular debris and environmental contaminants that can also be collected along with the biological sample. Separation of substrate 440A from substrate 440B provides a convenient way to use the nucleic acid for further genotyping analysis but also can provide a medium for long term storage or archiving of the nucleic acid sample.

Figure 5A:
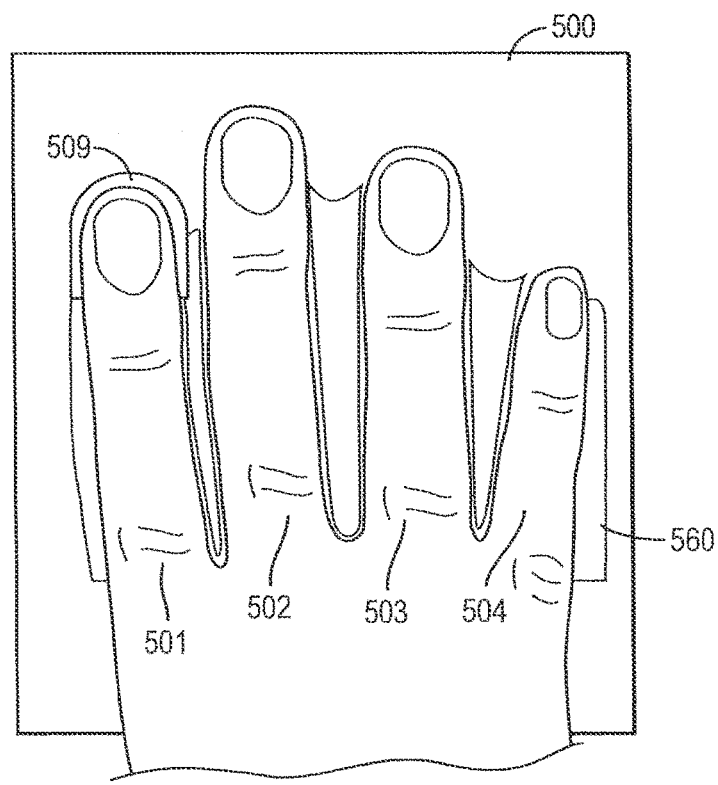
FIG. 5A-5C illustrate a system having a housing, a substrate and a cross-sectional view of the systems for collecting a ridge and valley signature and nucleic acid of an individual, in accordance with various embodiments.

In certain embodiments, a system as in FIG. 5 can be used for the simultaneous collection of a nucleic acid sample and a ridge and valley signature. The system of FIG. 5A has an imaging component having a housing 500 containing a substrate 560 for collecting a biological sample from fingers 501, 502, 503, and 504. At the same time, scanning surface 509 collects the ridge and valley signature from a finger tip positioned upon surface 506 through which scanning element 509 illuminates and collects the ridge and valley signature. Scanning element 509 is in electronic connection with scanner mechanism 511. Scanner mechanism 511 provides the necessary electronics to convert the image that scanner 509 obtains into a digitized electronic form of the ridge and valley signature. The electronic ridge and valley signature may be stored locally, or communicated to a remote database for storage or other processing by scanner mechanism 511 or by other elements in electronic connection with scanner mechanism 511.

Figure 5B:
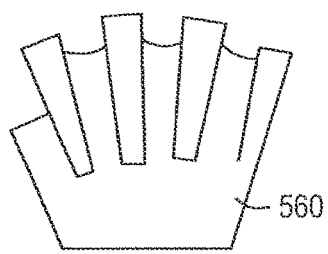
Figure 5C:
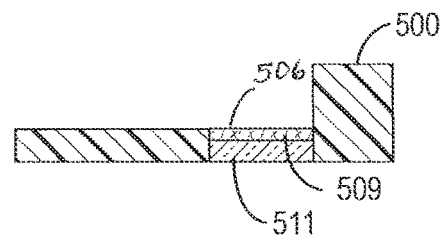

The substrate 560, as shown in FIG. 5B, can further have a lysis solution applied to it for extraction of nucleic acid from the biological sample collected from the skin of the fingers in contact with substrate 560. After removal of the finger from the lysis solution, the biological sample may be retrieved for archiving, testing or mailing to a testing laboratory. FIG. 5C illustrates a sectional view of the housing 500, scanning element 509 having a surface 506, and scanner mechanism 511.

In further embodiments of the present teachings, FIG. 6A illustrates a system having an imaging component having a housing 600 in which a finger is placed within the illustrated depression (not numbered) atop a substrate 608 located proximal to a trough 607 containing a lysis solution (not numbered), which may be used in the methods of the invention. In some embodiments, the trough 607 is above the scanner 609 which can match the barcode 611 associated with substrate 608 to the ridge and valley signature obtained by scanner 609. After the imaging of the at least one ridge and valley signature, the finger is removed from the trough containing the lysis solution substrate. the biological sample which had been collected in the lysis solution may then be retrieved for archiving, testing or mailing to a laboratory for testing. In other embodiments, an aliquot of the lysis solution in trough 607 is spotted on a paper such as FTA® paper and dried. A punch (1.2 mm) is taken from the paper and placed into a lysis solution for extraction of the nucleic acid and subsequent analysis for nucleic acid markers such as DNA markers for STRs, Indels, SNPs and combinations thereof as well as DNA sequencing methods. Reagents for analyzing nucleic acids are commercially available such as the AmpF/STR® Identifiler® Direct PCR Amplification Kit (Applied Biosystems, Foster City, Calif.) and the Power-Plex® 18D System (Promega Corp. Madison, Wis.) in conjunction with Prep-n-Go™ Buffer (Applied Biosystems) following the manufacturer's instructions.

In further embodiments the Prep-n-Go buffer may be used as the lysis solution in the above illustrations and further contains an enzyme and/or a surfactant for extraction of the nucleic acid from the illustrated substrates or gels.

Figure 7:
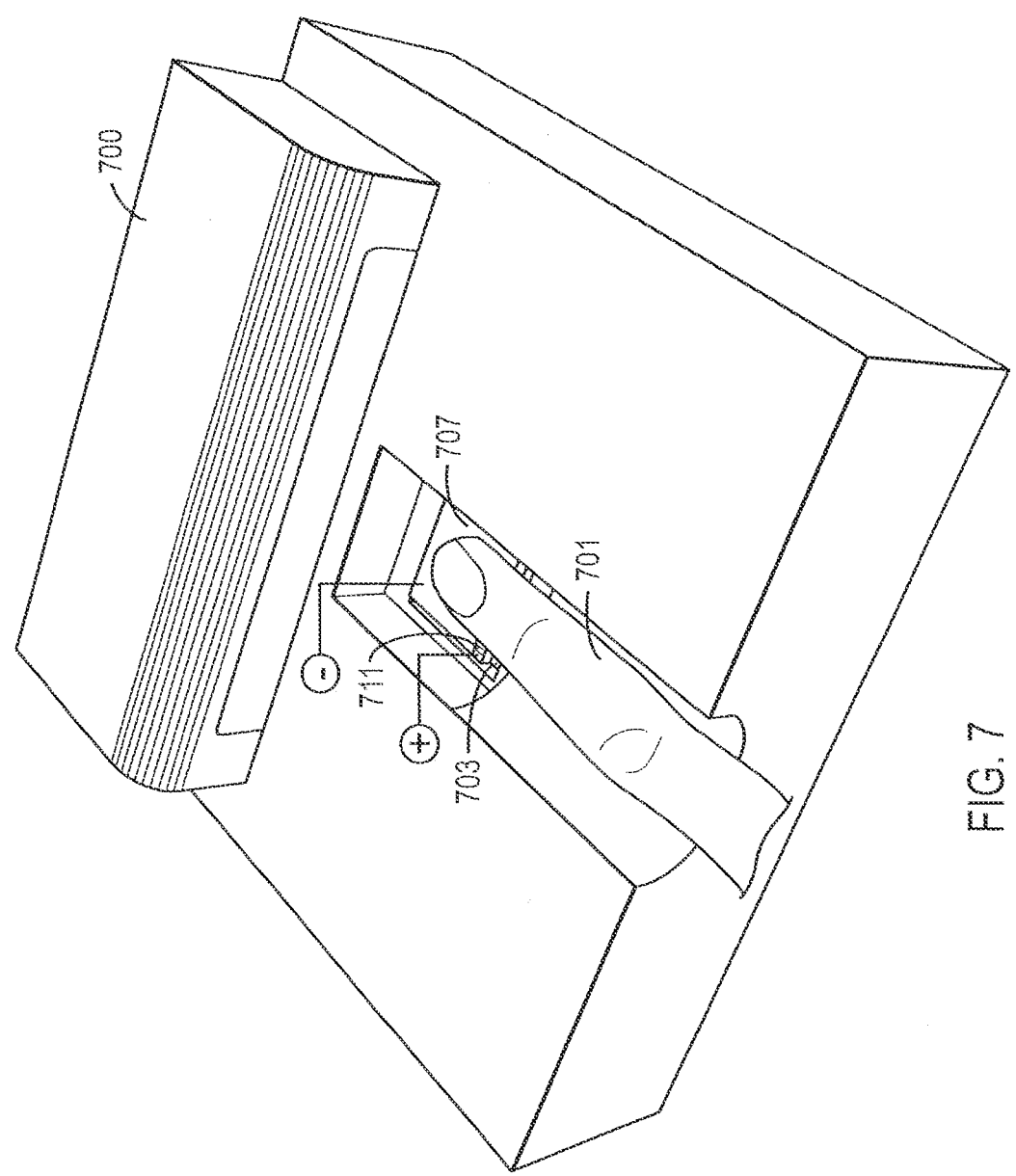
FIG. 7 illustrates a system having a housing and a substrate for scanning a finger or toe for collecting a ridge and valley signature and collecting nucleic acid of an individual, in accordance with various embodiments.

In further embodiments, FIG. 7 illustrates a system of the present teachings for simultaneous collection of a nucleic acid sample and a ridge and valley signature comprising: a.) an imaging component having a housing, wherein the housing comprises: i. a recessed area, wherein the depressed area comprises: 1. a substrate amenable to electrophoresis, wherein the biological sample is collected; and 2. a scanning surface positioned under the substrate, wherein a ridge and valley signature is captured; and 3. a support for the scanning surface. In certain embodiments the substrate can have a barcode, the scanning surface 703 below substrate 707 illuminated the scanning surface 703 to capture the ridge and valley signature and the substrate 707 is a gel capable of extracting nucleic acid from the biological sample collected from finger 701 as the finger is withdrawn from the substrate. In other embodiments, the substrate is in communication with an electrophoresis apparatus (anode and cathode indicated) within housing 700 at a first edge of the substrate 707 at the anode electrical connection and a cathode electrical connection with a second edge of substrate 707, whereby at least one nucleic is migrated to a proximity of the second edge and away from a proximity of the first edge.

In various embodiments, the system collects at least one ridge and valley signature of an individual and a biological sample comprising nucleic acid simultaneously or collects in succession the signature and biological sample or, visa versa, the biological sample and the signature with the at least first imaging system, while requiring the individual to touch an apparatus only once.

Processor.

After collection of the at least one ridge and valley signature, the signature, in analog or digital format, can be transmitted to a database having a plurality of ridge and valley signatures, as well as any other physical biometric data collected and deemed suitable to transmission. In some embodiments, the system includes a processor configured to transmit the ridge and valley signature obtained from the individual to at least one database which retains ridge and valley signatures of individuals. In some embodiments the database is selected from the group consisting of a forensic, criminal, identity, child identity, missing persons, immigration, department of motor vehicles, terrorist, paternity, arrestee, convict database, access control or any combination thereof.

Identifier.

In still other embodiments of the present teachings, the system can further comprise an identifier for associating identifying information with the signature, biological sample, and, optionally a physical image, including any of a facial image, an iris image, a retinal image or an ear image of the individual. In some embodiments, the name of the individual is included in the identifier. The identifier may aid in correlating various collected samples and may preclude sample mix-up and human error as may occur with nonsystematic sample labeling for identifying collected data and samples. In various embodiments, the identifier is alphanumeric, graphical, magnetic, or electromagnetic. In some embodiments, the identifier is a barcode. In various embodiments, the substrate comprises an identifier. In other embodiments, a support comprises an identifier. In yet other embodiments, both the substrate and the support comprise the identifier to aid in correlating the collected sample and images. If more than one imaging component is included in the system, the same identifier may be used on all the collected data and samples of one individual.

Other Components.

In yet other embodiments, the system additionally includes amplification, purification and separation components which may be used to: obtain the at least one nucleic acid from the biological sample; purify the at least one nucleic acid before further amplification and analysis; amplify the at least one nucleic acid; separate the amplified at least one nucleic acid; and detect the amplified at least one nucleic acid. Any or all of these additional components may be used to identify the individual. The biological sample containing at least one nucleic acid may be subjected to subsequent analysis for nucleic acid markers such as DNA markers for STRs, Indels, SNPs and combinations thereof as well as DNA sequencing methods. Reagents for analyzing nucleic acids are commercially available such as the AmpF/STR® Identifiler® Direct PCR Amplification Kit (Applied Biosystems, Foster City, Calif.) and the PowerPlex® 18D System (Promega Corp. Madison, Wis.) in conjunction with Prep-n-Go™ Buffer (Applied Biosystems) following the manufacturer's instructions.

Kits.

The invention also provides for kits. A kit may contain one or more substrate of any of the various substrates described herein, where the substrate may or may not include a support. The kit may include storage enclosures for the substrate containing the biological sample and/or the at least one nucleic acid, and may also contain directions for archiving. The kit may also contain a lysis solution for extraction of the at least one nucleic acid. The kit may contain one or more protease for extraction of the at least one nucleic acid from the biological sample collected from the skin of the individual. The kit may contain other reagents for reactions such as PCR amplification reactions or analyses such as STR, SNP or Indel analyses. The kit may further include mailing enclosures for the substrate containing the biological sample or at least one nucleic acid. In some embodiments, the kit may include instructions for use, storage, processing and for relaying the image of the at least one ridge and valley signature to a database.

Methods.

The invention provides for methods of collecting a biological sample comprising at least one nucleic acid sample and at least one ridge and valley signature. In some embodiments, the methods include identifying the individual. In various embodiments, the method for collection of a biological sample comprising at least one nucleic acid and at least one ridge and valley signature of an individual includes providing at least a first imaging component. The at least imaging component is configured to provide an energy wave and comprises a scanning surface configured to permit the energy wave to penetrate the scanning surface. The method includes providing a substrate configured to collect the biological sample from an appendage of the individual. The method includes the steps of positioning an appendage of the individual on the scanning surface and in contact with the substrate; collecting the at least one ridge and valley signature from the appendage imaged by the energy wave; and withdrawing the appendage from the scanning surface while exerting pressure on the substrate, thereby collecting the biological sample. The appendage may be a finger, toe, palm of a hand or sole of a foot.

In some embodiments the method may also include the step of transmitting the at least one ridge and valley signature of the individual to at least one database containing ridge and valley signatures, which may be a forensic, criminal, identity, child identity, missing persons, immigration, department of motor vehicles, terrorist, paternity, arrestee, convict database, access control database or any combination thereof.

The method may further include the step of providing an identifier to associate the biological sample of the individual with the at least one ridge and valley signature of the individual, wherein the identifier is alphanumeric, graphical, magnetic, or electromagnetic. In some embodiments, the identifier is a barcode.

The method may further include comprising the step of subjecting the biological sample to at least one of a polymerase chain reaction, a DNA sequencing reaction, STR analysis, SNP analysis, or Indel analysis. In some embodiments, this method may identify an individual.

The method may also include the step of archiving the substrate containing the biological sample. In some embodiments, the substrate containing the biological sample or the at least one nucleic acid may be sent to another facility for archiving or for processing. In any of the methods, the at least first imaging component may be an optical scanner or a capacitance scanner.

In some embodiments, the optical scanner comprises a LED, laser diode, incandescent light source, or a multispectral imager. The at least first imaging component may alternatively a camera, an active pixel imager, a CMOS imager, an imager that images in multiple wavelengths, a CCD camera, a photo detector array, and a TFT imager. The at least one ridge and valley signature may be collected electronically. The scanning surface of the at least first imaging component may be formed from a material selected from a plastic, a polyolefin, a polystyrene, a metal, a metal alloy, a glass, a silicon or combinations thereof. In some embodiments, the material of the scanning surface is transparent or translucent.

In various embodiments, the substrate may further include a support. In some embodiments, the support is formed from a material selected from a polymer, a metal, a metal alloy, a glass, a silicon material or a combination thereof. The support may be transparent or translucent.

In some embodiments of the method, the substrate includes a paper material selected from Whatman® paper, including W-903 paper, FTA™ paper, FTA™ Elute paper, FTA™ DMPK paper, Ahlstrom A-226 paper, M-TFN paper, FTA® paper, FP705™ paper, Bode DNA collection paper, nitrocellulose paper, nylon paper, cellulose paper, Dacron paper, cotton paper, and polyester papers, and combinations thereof. In some embodiments, the paper substrate may further include a lysis solution. In other embodiments, the paper substrate may further include microneedles.

In the methods, the substrate may be a gel. In some embodiments, the gel substrate may be a starch, an agarose, an alginate, a carrageenan or a synthetic polymer gel, or a mixture thereof. In some embodiments, the gel substrate may further include a lysis solution. In some embodiments the gel substrate may be configured to permit electrophoresis. In various embodiments, the gel substrate may be transparent or translucent. The method may include the step of electrophoresing the biological sample on the gel thereby concentrating the at least one nucleic acid.

In various embodiments of the method, the substrate may be a lysis solution and may be contained in a support. In some embodiments, the lysis solution may include proteinase K. In other embodiments, the lysis solution includes an enzyme selected from a serine protease, a cysteine protease, an acid protease, a metalloprotease, an aminopeptidase, a carboxypeptidase, a pancreatic proteolytic enzyme and a keratinase.

In various embodiments, at least a portion of the substrate is positioned over the scanning surface and is transparent or translucent. In other embodiments, at least a portion of the support is positioned over the scanning surface and is transparent or translucent. In yet other embodiments, at least a portion of the substrate is positioned proximal to the scanning surface. In some other embodiments, the support is attached to the substrate. The attached support may be positioned upon the scanning surface and permit imaging and collection of the at least one ridge and valley signature through the support. In other embodiments, the support is not attached to the substrate and is positioned proximal to the scanning surface. When a lysis solution is the substrate and is contained within a support, the support and the lysis solution may be positioned proximal to the scanning surface. In some embodiments, the substrate and/or support may permit four fingers to be positioned within the substrate and/or support. Alternatively, when the lysis solution substrate is contained within a support that is transparent or translucent, at least a portion of the substrate and the support may be positioned upon the scanning surface. This arrangement of substrate and support may permit the imaging and collection of the at least one ridge and valley signature through the lysis solution substrate and the support.

In other embodiments of the method the method further includes the step of vibrating the substrate as the appendage of the individual is withdrawn from the scanning surface while exerting pressure upon the substrate.

The steps of collecting the biological sample and collecting the at least one ridge and valley signature may be performed at the same time or may be performed sequentially, in any order. The imaging component may be an optical scanner or a capacitance scanner, wherein the energy wave is a light wave or an electrical wave.

Those having ordinary skill in the art will understand that many modifications, alternatives, and equivalents are possible. All such modifications, alternatives, and equivalents are intended to be encompassed herein.

EXAMPLES

The following procedures are representative of procedures that can be employed for the collection, analysis and archiving/cataloging biological samples and biometric data from an individual.

Example 1

This example illustrates the feasibility of capturing DNA from fingertips using a liquid phase. A fingertip was brought into contact with a liquid and DNA was transferred from the fingertip to the liquid. The liquid phase was an aqueous solution or can be another solvent. Alternatively, the liquid phase can contain chemical or biological reagents that help to extract biological fluids from the fingertips. The extracted biological fluids can contain cells or free DNA. The liquid phase used to harvest DNA from the fingertips can contain reagents that lyse cells, stabilize DNA, encourage transfer of the DNA from the fingers to the liquid phase, or induce the skin on the finger to release DNA or cells containing DNA.

Liquid phase collection of DNA from fingertips was tested using a prototype lot of Prep-n-Go™ buffer (Life Technologies, Foster City, Calif.) that was formulated without sodium azide. Protease K was added to the Prep-n-Go™ buffer for a final concentration of 1 mg/mL.

Example 1A 500 uL of Prep-n-Go™/PK was pipetted into a 4 cm×4 cm polystyrene weigh boat (VWR p/n 89106-764). A single finger of an individual was placed in the solution for 10 seconds. Nine individuals were tested. The resulting finger extraction solution for each individual was transferred by pipette to a 1.5 mL tube. Each of the samples was heated to 100 C for 10 minutes to inactivate the PK.

The DNA extracted into the Prep-n-Go™/PK solution was analyzed with the AmpFlSTR® Identifiler® Direct kit (Life Technologies, Foster City, Calif.). PCR was performed using 4 ul of finger extraction solution. Each sample was then added to a well containing 25 uL Identifier® Direct mastermix and thermocycled under the following conditions: 95 C/11 m, 27 cycles of (94 C/20 s, 59 C/2 m, 72 C/1 m), 60 C/25 min and 4 C—hold. After thermal cycling the PCR reactions were mixed with GeneScan® 500 size standard and deionized formamide and analyzed using a ABI 3500xl capillary electrophoresis instrument using the following conditions: Oven: 60 C, Prerun: 15 kV, 180 s, Injection: 1.2 kV, 24 s, Run: 15 kV, 1210 s, Capillary length: 36 cm, Separation polymer: POP4™ polymer and Dye set: G5. Complete STR profiles were obtained from all samples tested. The 4 uL extraction solution added directly to the STR reaction gave excellent peak height with very good intracolor balance.

Figure 8A:
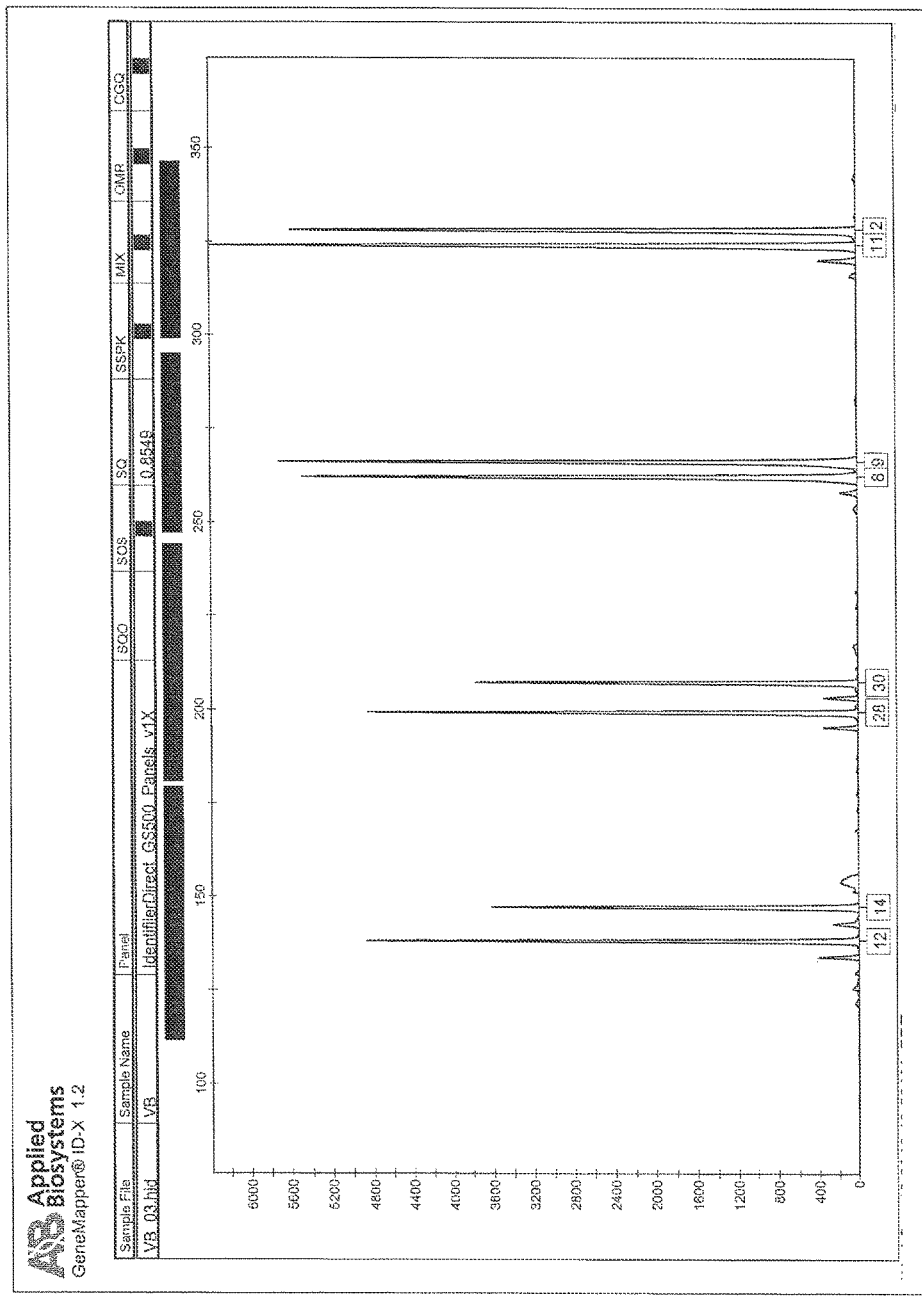
FIGS. 8A-D are graphical representations of a STR analysis obtained from a first individual according to the systems and methods of the invention.
Figure 8B:
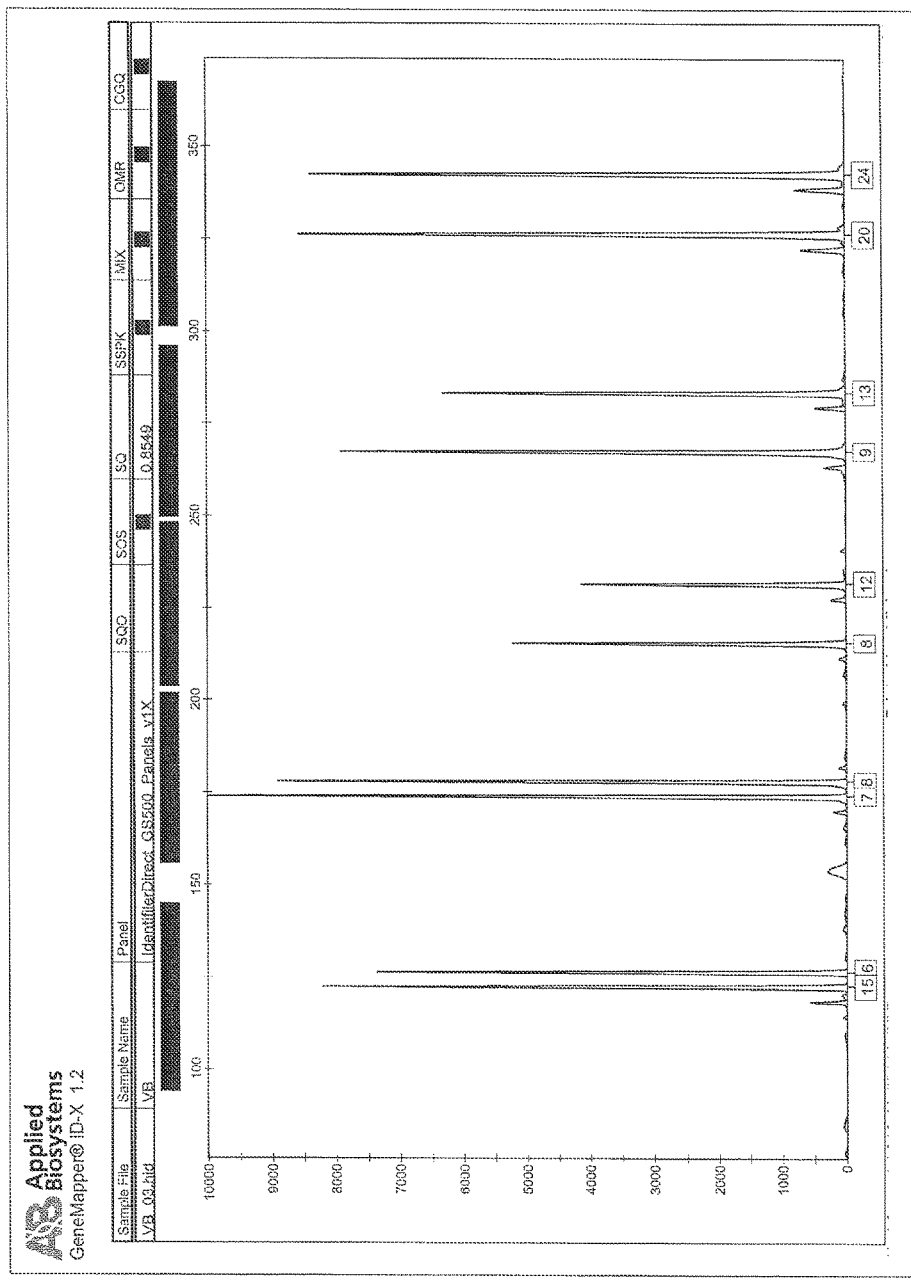
Figure 8C:
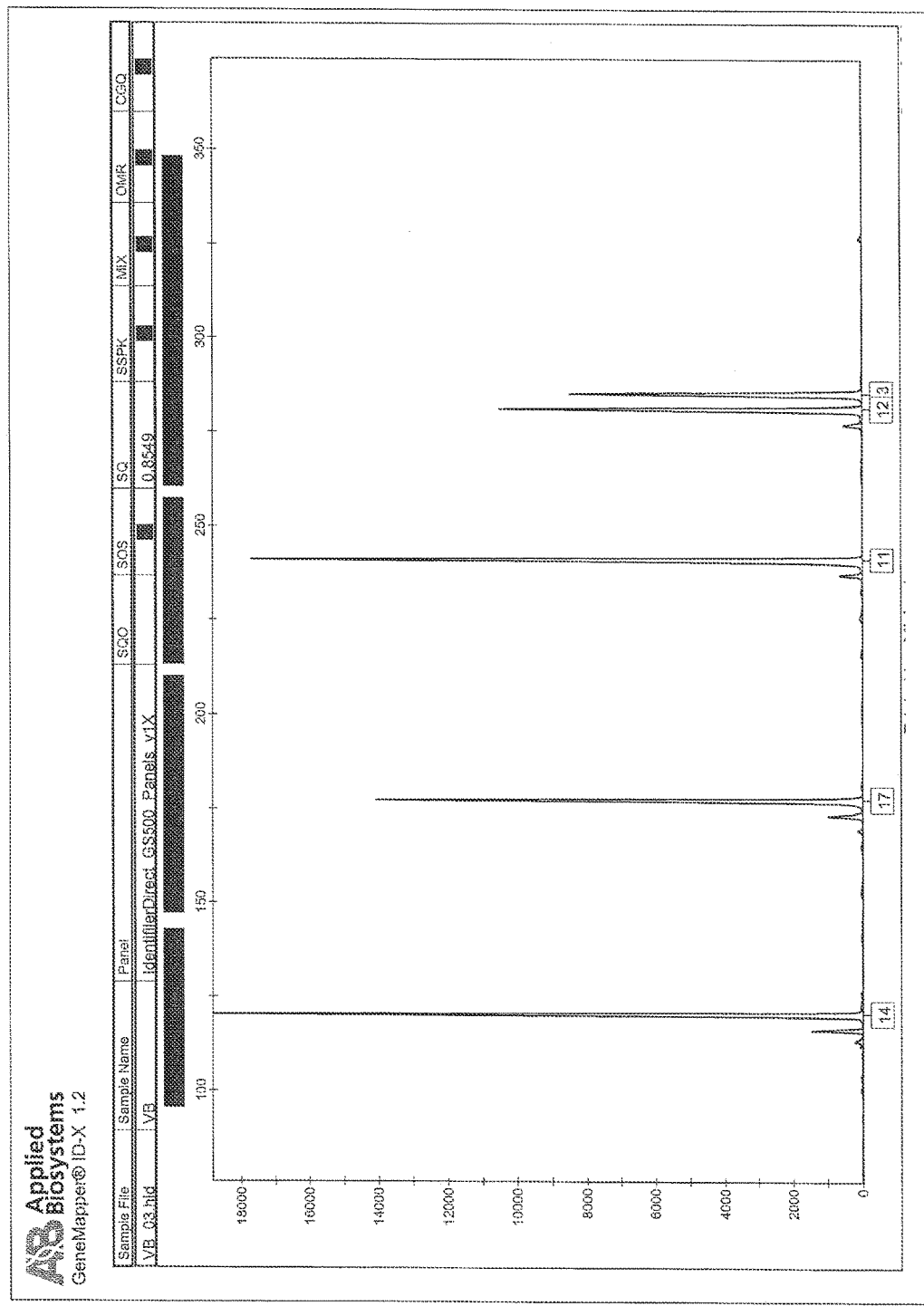
Figure 8D:
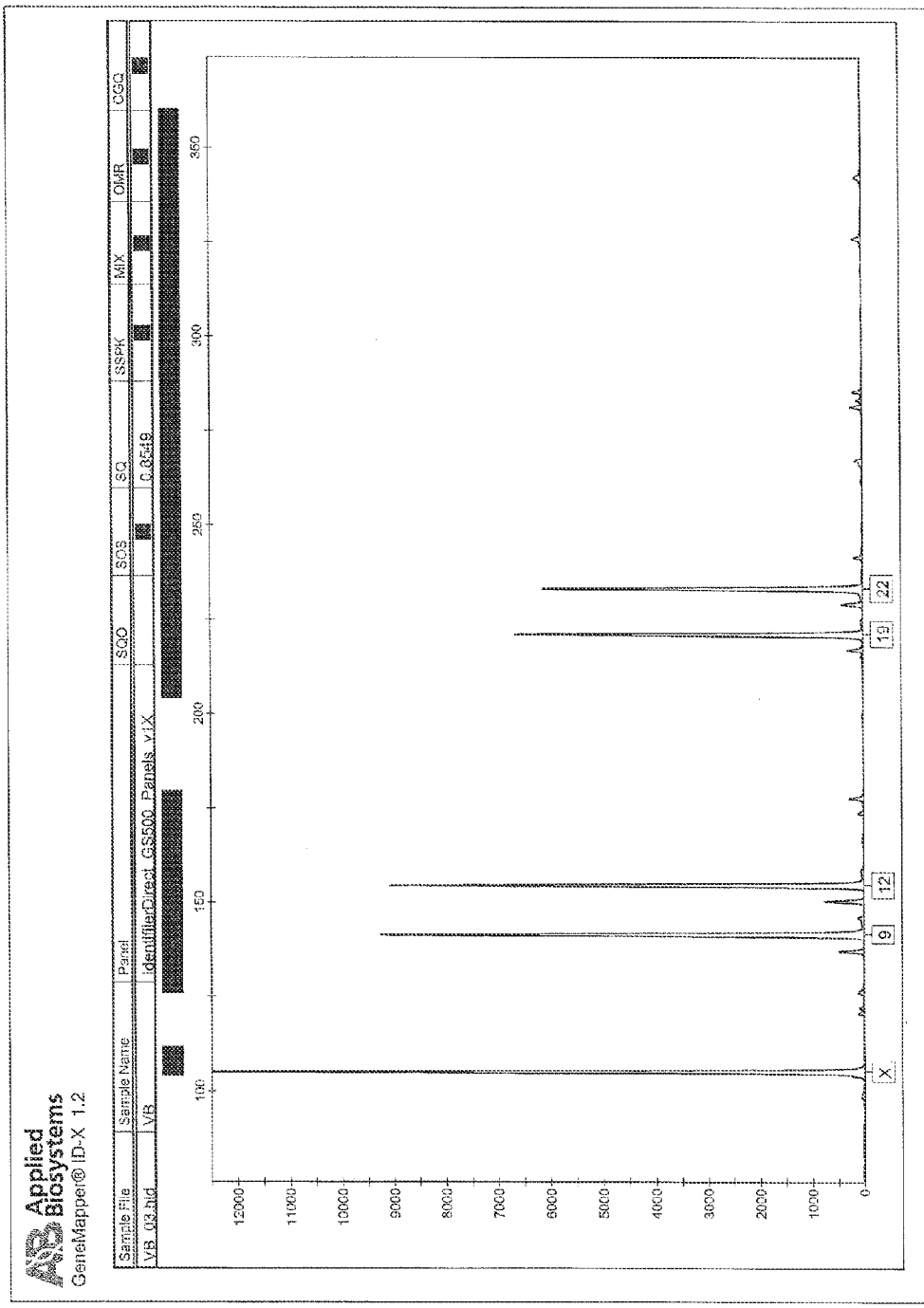
Figure 9A:
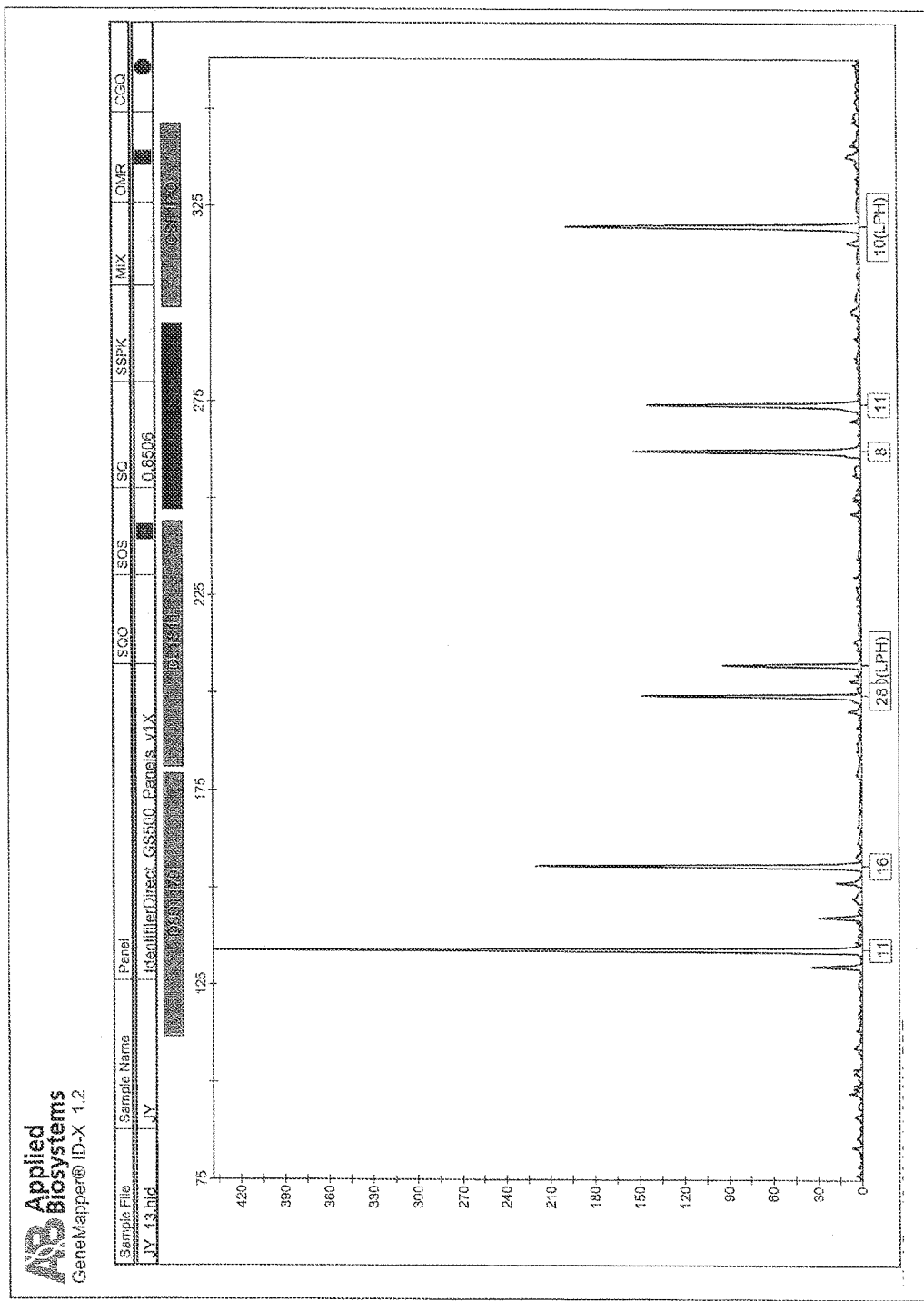
FIGS. 9A-D are graphical representations of a STR analysis obtained from a second individual according to the systems and methods of the invention.
Figure 9B:
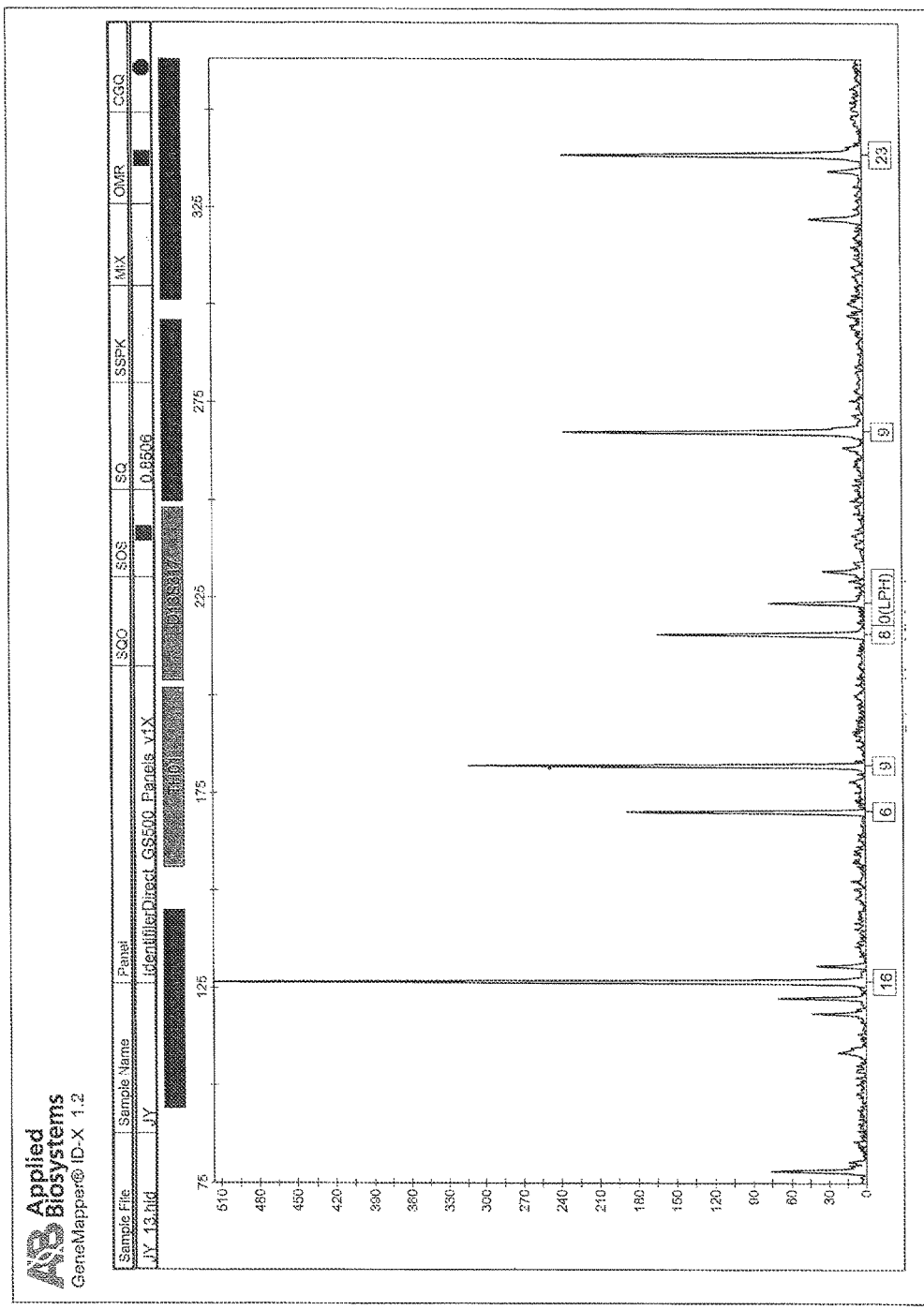
Figure 9C:
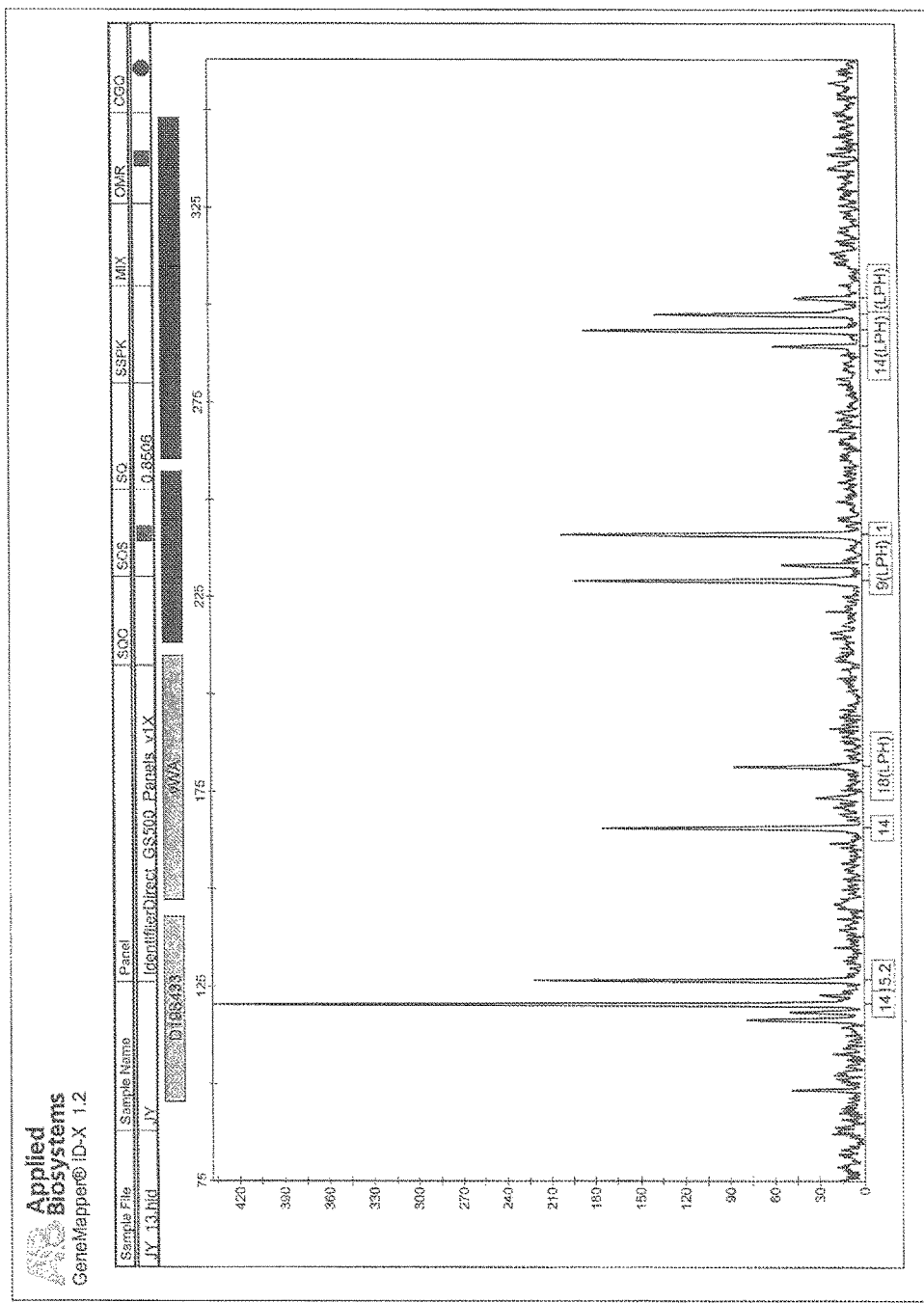
Figure 9D:
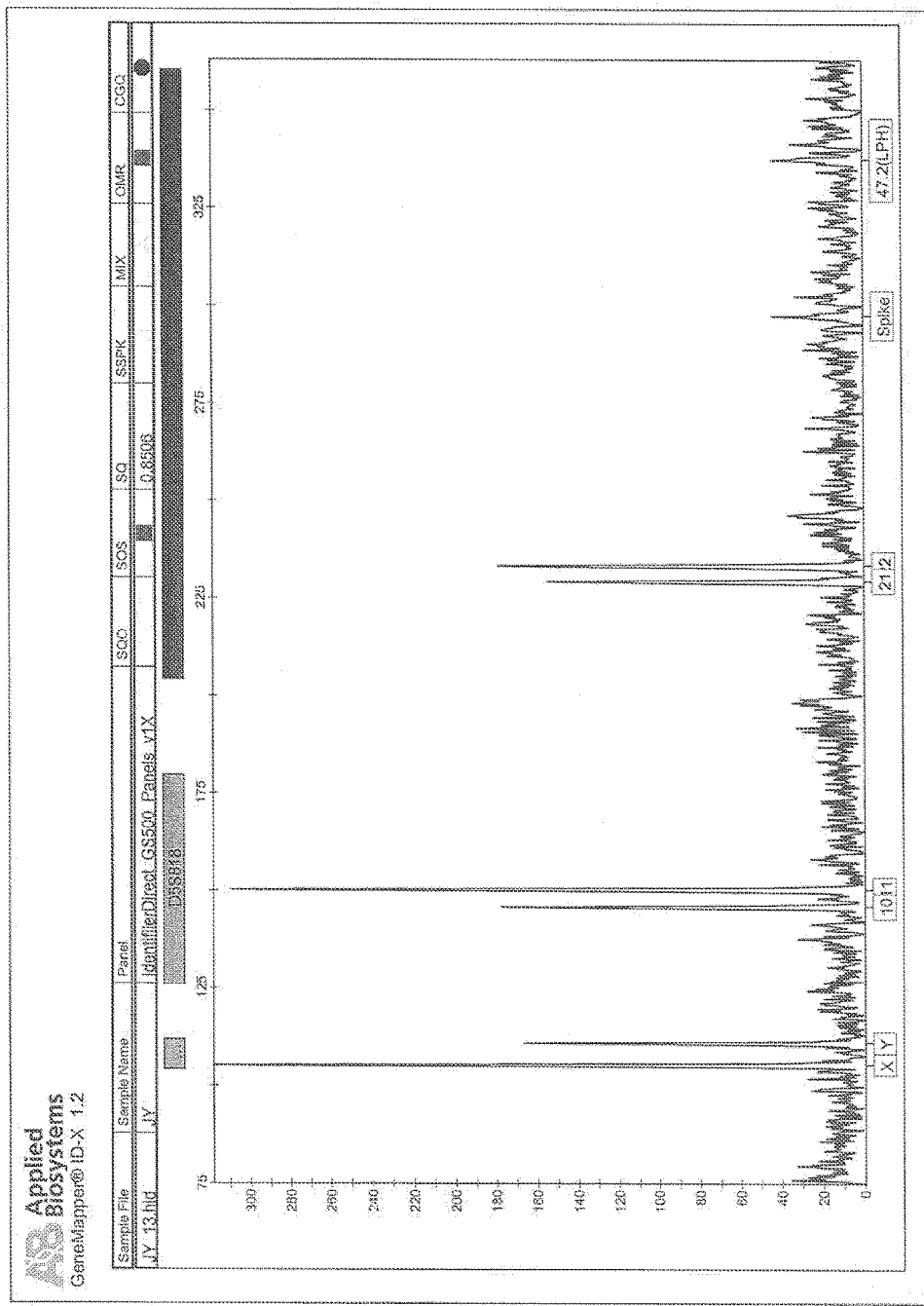

The resulting STR electropherograms were analyzed using GeneMapper® ID-X software (Applied Biosystems, Foster City, Calif.). Full STR profiles for all 15 STR markers and the sex determination marker Amelogenin were obtained for seven of the nine donors. Partial profiles were obtained for the remaining two donors. The STR profiles for two individuals obtaining full profiles are shown in FIGS. 8A-D and FIGS. 9A-D, demonstrating that definitive profiles are produced. FIGS. 8A-D represent the STR panel for the first individual where FIG. 8A shows, from left to right the alleles for D8S1179, D21S11, D7S820, and CSF1PO; FIG. 8B shows D3S1358, TH01, D13S317, D16S539, and D2S1338; FIG. 8C shows D19S433, vWA, TPOX, and D18S51; and FIG. 8D shows Amelogenin, D5S818, and FGA. FIGS. 9A-D represent the STR panel for the second individual where FIG. 9A shows, from left to right the alleles D8S1179, D21S11, D7S820, and CSF1PO; FIG. 9B shows D3S1358, TH01, D13S317, D16S539, and D2S1338; FIG. 9C shows D19S433, vWA, TPDX, and D18S51; and FIG. 9D shows Amelogenin, D5S818, and FGA. Peaks labeled "(LPH)" or "Low Peak Height" represent peaks lower than a preselected peak height, which may be an arbitrary number. The results clearly show a definitive profile, despite the arbitrary labeling.

Example 1B 200 uL of Prep-n-Go™/PK was pipetted directly onto the glass platen of an optical fingerprinting device (Lego OEM). A single finger of an individual was placed in the solution while the fingerprint was recorded. The resulting finger extraction solution was transferred by pipette to a 1.5 mL tube. The sample was heated to 100 C for 10 minutes to inactivate the PK.

Figure 10A:
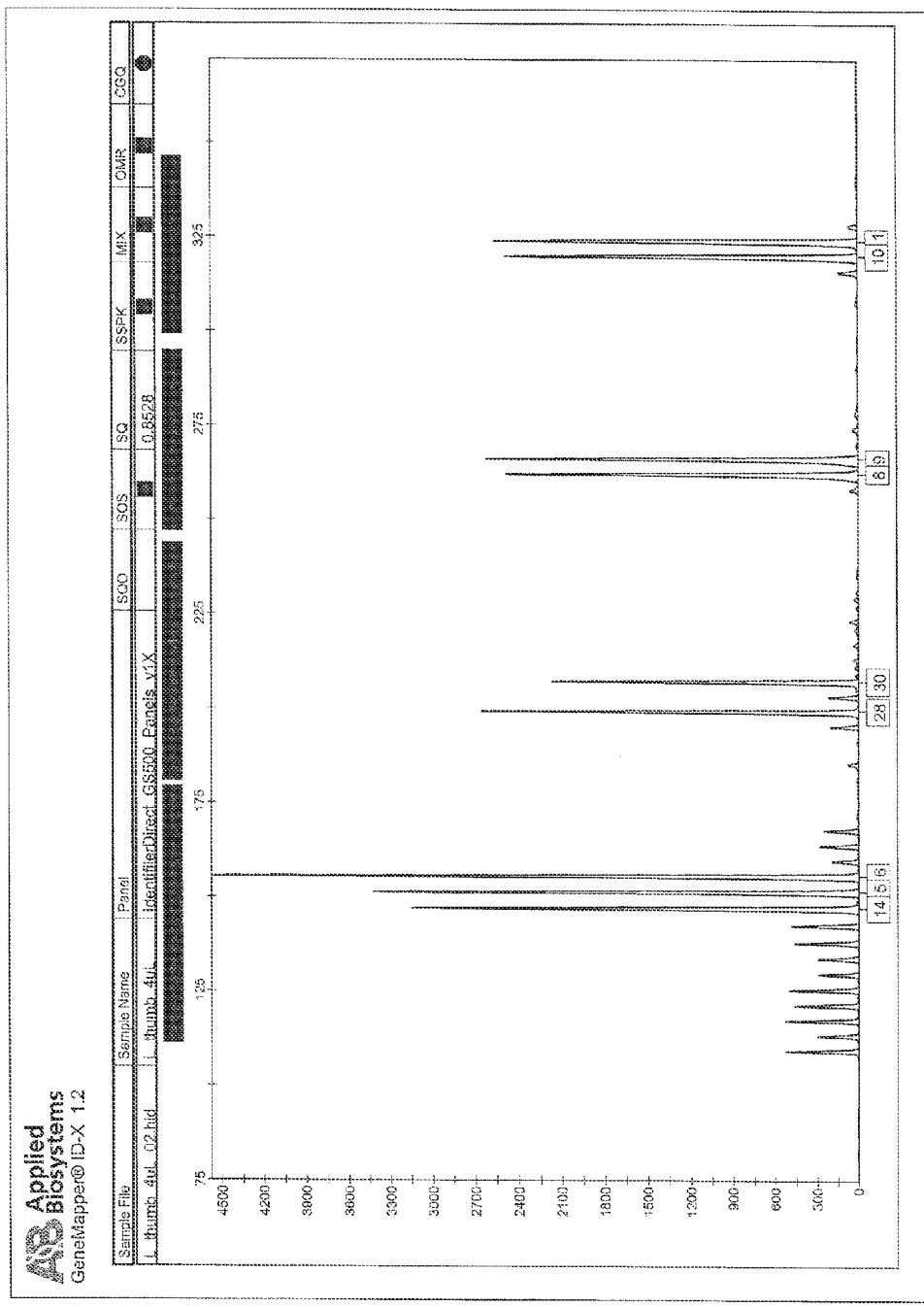
FIGS. 10A-D are graphical representations of a STR analysis obtained from an individual according to the systems and methods of the invention.
Figure 10B:
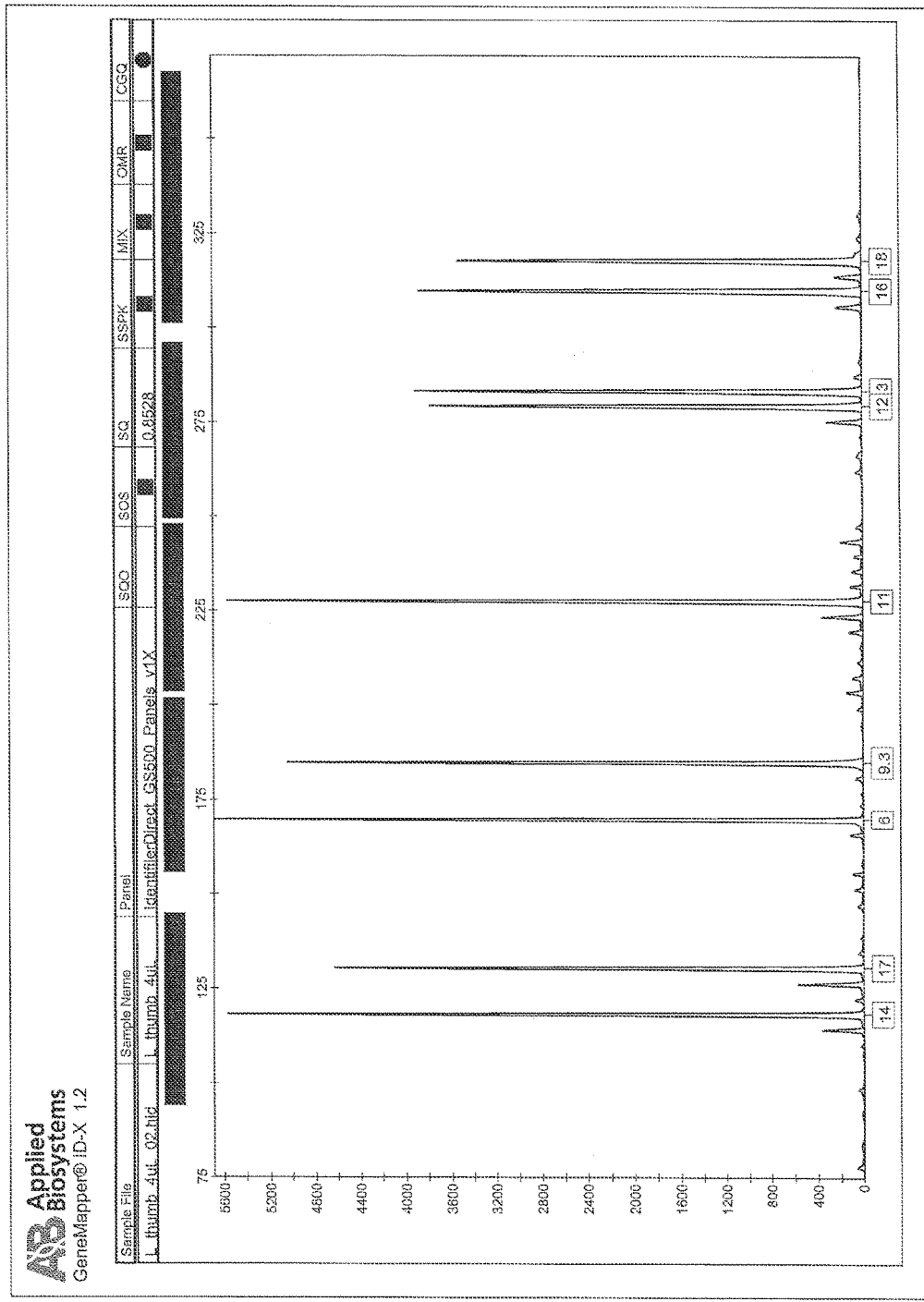
Figure 10C:
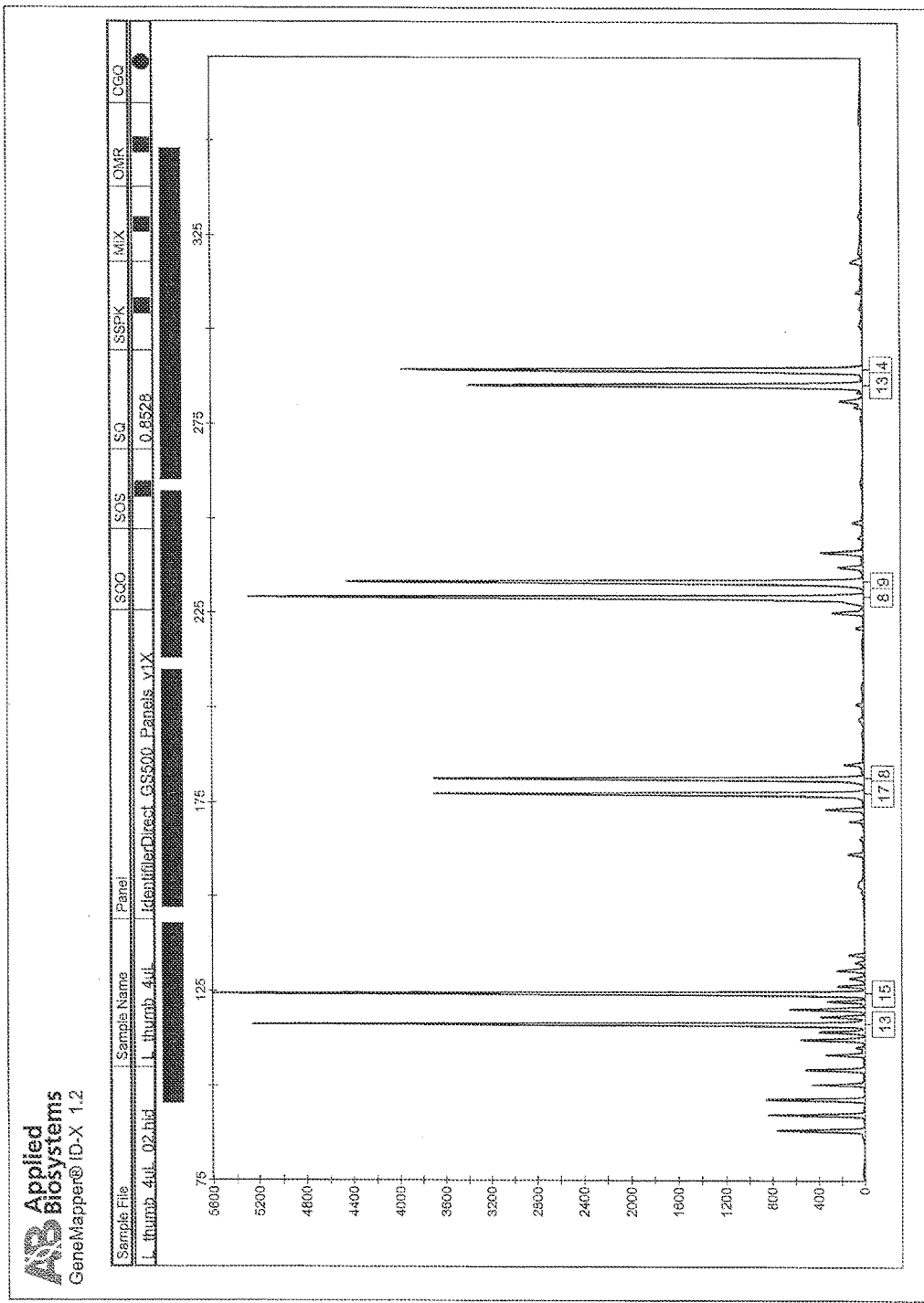
Figure 10D:
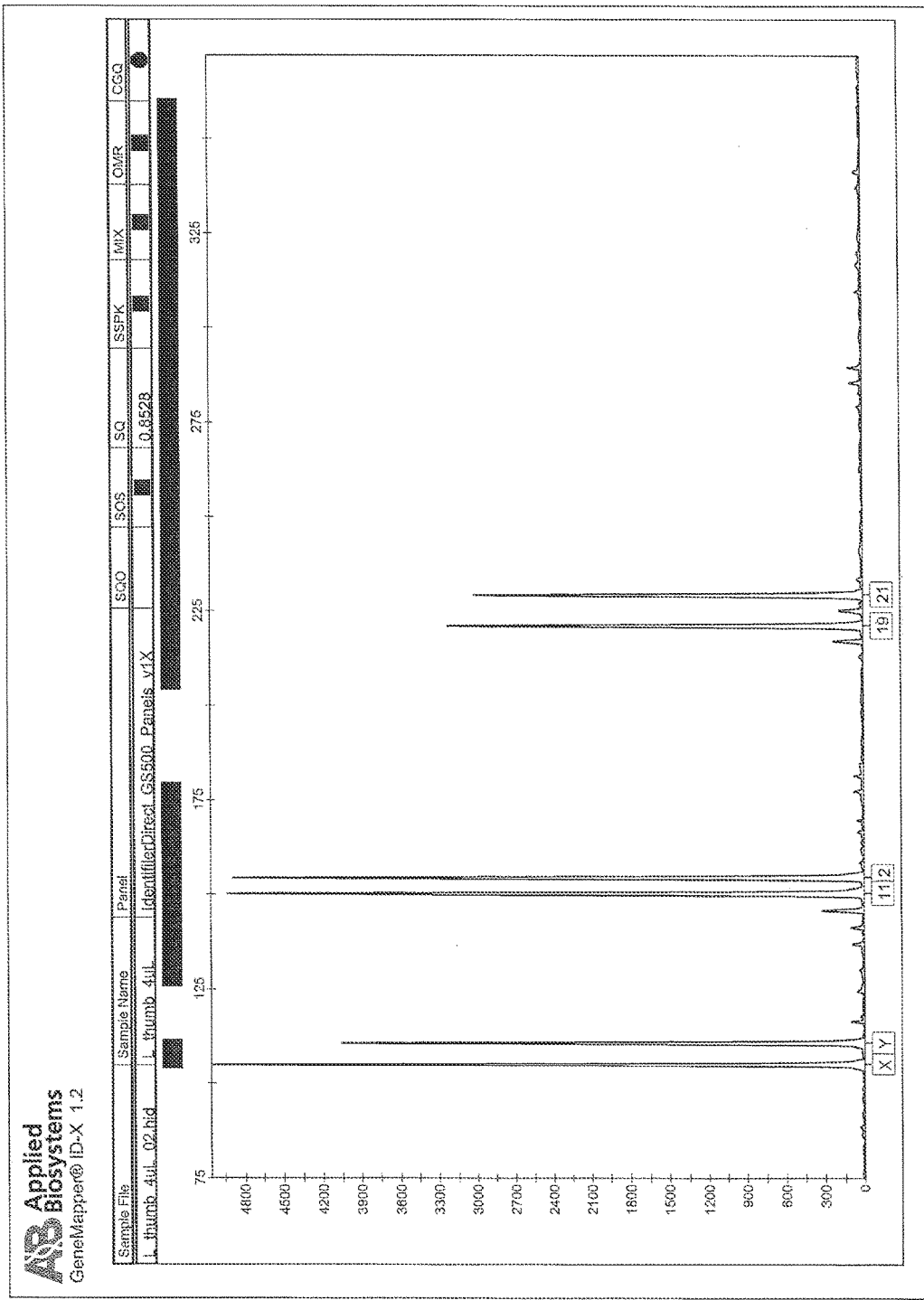

PCR was performed using 4 ul of finger extraction solution, and performed as in Example 1A. A full STR profile was produced with high signal strength, as shown in FIG. 10A-D. FIGS. 10A-D represent the STR panel for the second individual where FIG. 10A shows, from left to right the alleles D8S1179, D21S11, D7S820, and CSF1PO; FIG. 10B shows D3S1358, TH01, D13S317, D16S539, and D2S1338; FIG. 10C shows D19S433, vWA, TPDX, and D18S51; and FIG. 10D shows Amelogenin, D5S818, and FGA.

Figure 11:
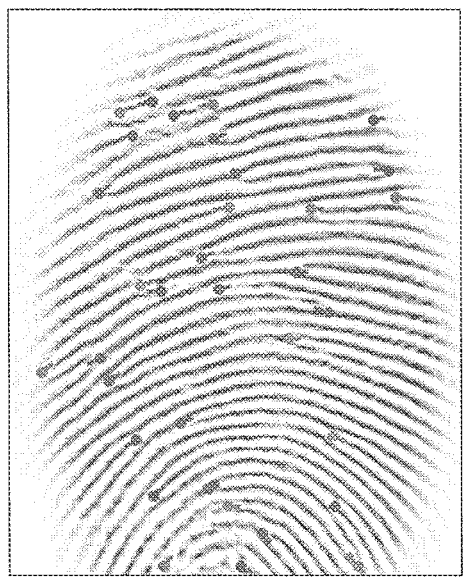
FIG. 11 is a graphical representation of a fingerprint obtained simultaneously with a biological sample from an individual.

While displaying some contaminants, the identity of the individual may be distinctly defined. The fingerprint obtained in this experiment is shown in FIG. 11 and is of high quality.

Example 2

The feasibility of capturing DNA and fingerprints at the same time using a substrate having a support attached to a substrate is demonstrated. The support is a film and the substrate is filter paper, as shown in FIG. 1B. The film material allows the collection of fingerprint, while filter paper strip allows the collection of DNA material. The size of the film is chosen to accommodate a fingerprint. The width of the filter paper may be less than about 3 mm to allow DNA material to be concentrated on the paper strip. The support is positioned upon the scanning surface and the substrate thereby is located proximally to the substrate. The collection of DNA material is accomplished by first positioning a finger upon the film to take a fingerprint, and then the finger is withdrawn with pressure across the substrate to collect the DNA material.

The collection of DNA material on a DNA-fingerprint device was tested by two individuals using a prototype DNA-fingerprint device with film (transparency film pp2200 from 3M) dimension of about 2 cm by about 2.5 cm and filter paper stripe (Whatman 3030-6189) dimension of about 2 cm by about 3 mm.

For DNA analysis, the filter paper strip was detached from the film. Three 3 mm diameter punches were generated from the substrate strip and was placed directly into one well of a 96-well PCR plate. 25 uL AmpFlSTR® NGM SElect™ Express (Life Technologies, Foster City, Calif.) PCR reaction mix was added to the wells containing paper punches. The thermo cycling conditions are 95 C/1 m, 29 cycles of (94 C/3 s, 59 C/16 sec, 65 C/29 sec), 60 C/5 min and 4

Figure 12A:
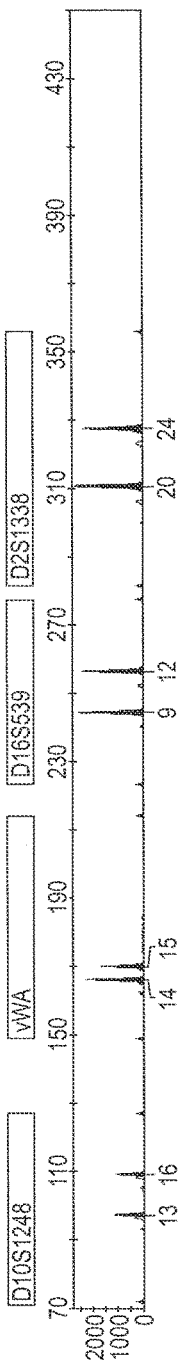
FIGS. 12A-D are graphical representations of a STR analysis obtained from a first individual according to the systems and methods of the invention.
Figure 12B:
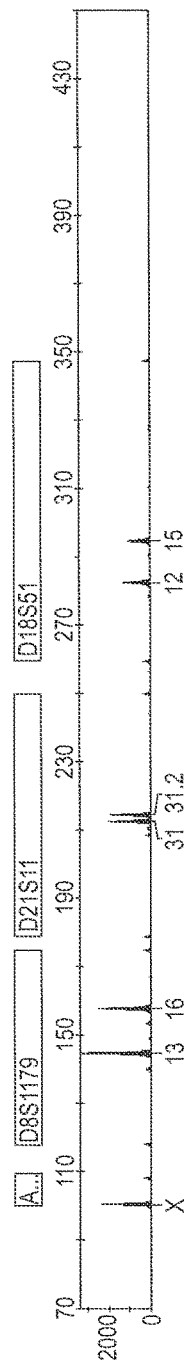
Figure 12C:
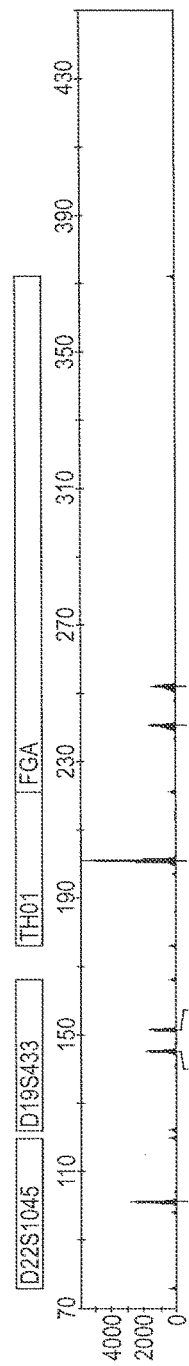
Figure 12D:
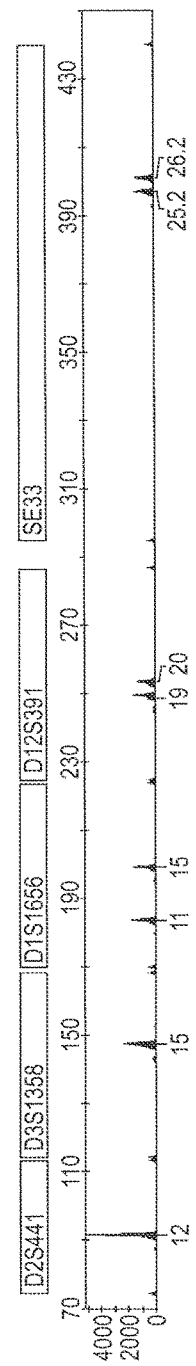
Figure 13A:
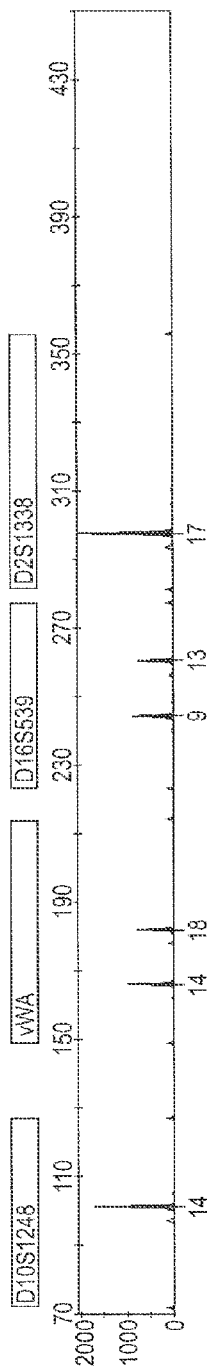
FIGS. 13A-D are graphical representations of a STR analysis obtained from a second individual according to the systems and methods of the invention.
Figure 13B:
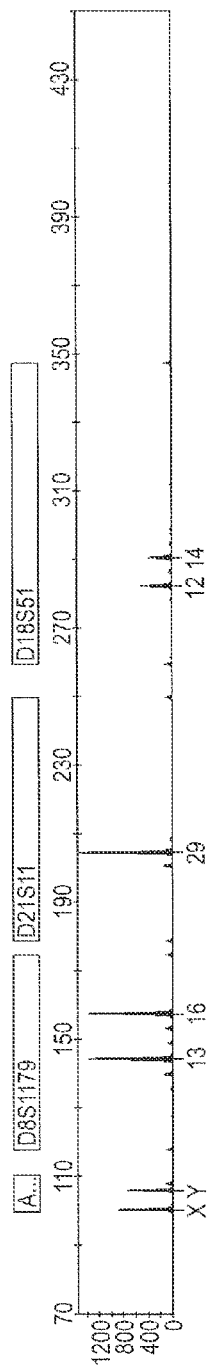
Figure 13C:
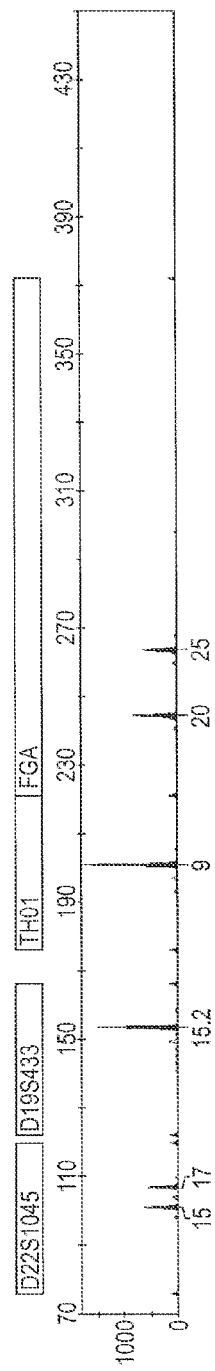
Figure 13D:
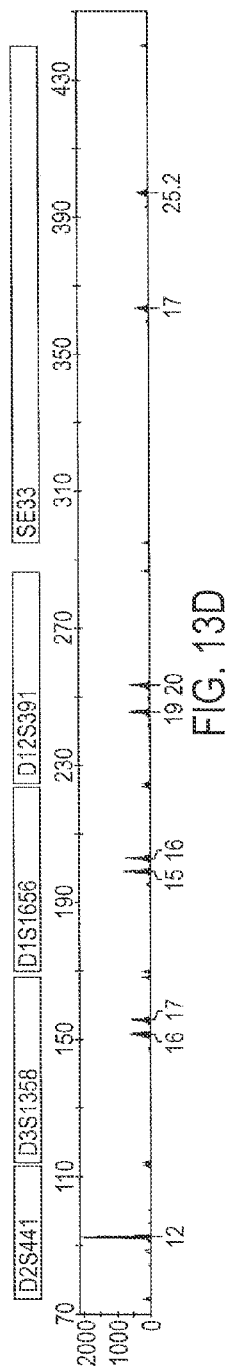

C—hold. After thermal cycling 1 uL PCR product from each sample was mixed with GeneScan® 500 size standard and deionized formamide and analyzed using a ABI 3100xl capillary electrophoresis instrument using the following conditions: Oven: 60 C, Prerun: 15 kV, 180 s, Injection: 3 kV, 10 s, Run: 15 kV, 1500 s, Capillary length: 36 cm, Separation polymer: POP4™ polymer and Dye set: G5. The resulting STR electropherograms were analyzed using GeneMapper® ID-X software (Applied Biosystems). Full STR profiles for all 16 STR markers and the sex determination marker Amelogenin were obtained, as shown in FIGS. 12A-D and FIGS. 13A-D. FIGS. 12A-D represent the STR panel for the first individual where FIG. 12A shows, from left to right the alleles for D10S1248, vWA, D16S539, and S2S1338; FIG. 12B shows Amelogenin, D8S1179, D21S11, and D18S51; FIG. 12C shows D22S1045, D19S432, TH01, and FGA; and FIG. 12D shows D2S441, D3S1358, DS1656, D12S39, and SE33. FIGS. 13A-D represent the STR panel for the second individual where FIG. 13A shows, from left to right the alleles for D10S1248, vWA, D16S539, and S2S1338; FIG. 13B shows Amelogenin, D8S1179, D21S11, and D18S51; FIG. 13C shows D22S1045, D19S432, TH01, and FGA; and FIG. 13D shows D2S441, D3S1358, DS1656, D12S39, and SE33.

While the foregoing specification teaches the principles of the present invention, with examples provided for the purpose of illustration, it will be appreciated by one skilled in the art from reading this disclosure that various changes in form and detail can be made without departing from the spirit and scope of the invention.

What is claimed:

1. A method for collection of a biological sample comprising at least one nucleic acid and at least one ridge and valley signature of an individual, comprising:
  a. providing at least a first imaging component configured to provide an energy wave and comprising a scanning surface configured to permit the energy wave to penetrate the scanning surface;
  b. providing a substrate configured to collect the biological sample from an appendage of the individual wherein the substrate is chemically modified with a chemical functional group selected from the group comprising an amino group, a chloromethyl group, a hydroxyl group, a carboxyl group and a quaternary amino group;
  c. positioning the appendage of the individual upon the scanning surface and in contact with the substrate;
  d. collecting the at least one ridge and valley signature from the appendage imaged by the energy wave; and
  e. withdrawing the appendage from the scanning surface, thereby collecting the biological sample upon the substrate.

2. The method of claim 1, further comprising the step of transmitting the at least one ridge and valley signature of the individual to at least one database comprising ridge and valley signatures selected from the group consisting of a forensic, criminal, identity, child identity, missing persons, immigration, department of motor vehicles, terrorist, paternity, arrestee, convict database, access control or any combination thereof.

3. The method of claim 1, further comprising the step of providing an identifier to associate the biological sample of the individual with the at least one ridge and valley signature of the individual, wherein the identifier is alphanumeric, graphical, magnetic, or electromagnetic.

4. The method of claim 3, wherein the identifier is a barcode.

5. The method of claim 1, further comprising the step of subjecting the biological sample to at least one of a polymerase chain reaction, a DNA sequencing reaction, STR analysis, SNP analysis, or Indel analysis.

6. The method of claim 1, further comprising the step of archiving the substrate containing the biological sample.

7. The method of claim 1, wherein the at least first imaging component is an optical scanner or a capacitance scanner.

8. The method of claim 7, wherein the optical scanner comprises a LED, laser diode, incandescent light source, or a multispectral imager.

9. The method of claim 1, wherein the scanning surface is formed from a material selected from a plastic, a polyolefin, a polystyrene, a metal, a metal alloy, a glass, a silicon or combinations thereof, optionally wherein the material of the scanning surface is transparent or translucent.

10. The method of claim 1, wherein the substrate comprises a gel.

11. The method of claim 1, wherein the substrate further comprises a support.

12. The method of claim 11, wherein the support is formed from a material selected from a plastic, a polyolefin, a polystyrene, a metal, a metal alloy, a glass, a silicon or combinations thereof.

13. The method of claim 11, wherein at least a portion of the support is positioned over the scanning surface and is transparent or translucent.

14. The method of claim 1, wherein at least a portion of the substrate is positioned over the scanning surface and is transparent or translucent.

15. The method of claim 1, wherein at least a portion of the substrate is positioned proximal to the scanning surface.

16. The method of claim 1, wherein the steps of collecting the biological sample and collecting the at least one ridge and valley signature are performed simultaneously.

17. The method of claim 1, further comprising the step of vibrating the substrate as the appendage is withdrawn.

* * * * *